(12) United States Patent
King et al.

(10) Patent No.: US 7,713,978 B2
(45) Date of Patent: May 11, 2010

(54) COMPOUNDS

(76) Inventors: Nigel Paul King, GlaxoSmithKline, Corporate Intellectual Property, Five Moore Dr., P.O. Box 13398, Research Triangle Park, NC (US) 27709; Jason Witherington, GlaxoSmithKline, Corporate Intellectual Property, Five Moore Dr., P.O. Box 13398, Research Triangle Park, NC (US) 27709

( * ) Notice: Subject to any disclaimer, the term of this patent is extended or adjusted under 35 U.S.C. 154(b) by 100 days.

(21) Appl. No.: 11/692,993

(22) Filed: Mar. 29, 2007

(65) Prior Publication Data
US 2007/0238737 A1  Oct. 11, 2007

(30) Foreign Application Priority Data
Mar. 31, 2006  (GB) ................... 0606526.2
Mar. 12, 2007  (GB) ................... 0704766.5

(51) Int. Cl.
*A61K 31/497*  (2006.01)
*C07D 405/00*  (2006.01)
(52) U.S. Cl. .................. 514/253.11; 544/364
(58) Field of Classification Search ............ 544/364; 514/253.11
See application file for complete search history.

(56) References Cited

U.S. PATENT DOCUMENTS

| 2004/0186148 | A1 | 9/2004 | Shankar et al. |
| 2004/0204422 | A1 | 10/2004 | Braje et al. |
| 2006/0030584 | A1 | 2/2006 | Hanson et al. |
| 2006/0160809 | A1 | 7/2006 | Braje et al. |

FOREIGN PATENT DOCUMENTS

| DE | 102005015040 A1 | 10/2006 |
| EP | 1159964 A2 | 12/2001 |
| EP | 1321463 A1 | 6/2003 |
| WO | 9827081 A1 | 6/1998 |
| WO | WO 98/27081 * | 6/1998 |
| WO | 9942465 A2 | 8/1999 |
| WO | 0005225 A1 | 2/2000 |
| WO | 0123374 A1 | 4/2001 |
| WO | 0157038 A1 | 8/2001 |
| WO | 0164642 A2 | 9/2001 |
| WO | 0236562 A2 | 5/2002 |
| WO | 02051397 A1 | 7/2002 |
| WO | 02074764 A2 | 9/2002 |
| WO | 02074768 A1 | 9/2002 |
| WO | 03030902 A1 | 4/2003 |
| WO | 2004052370 A2 | 6/2004 |
| WO | 2004076413 A2 | 9/2004 |
| WO | 2004087653 A2 | 10/2004 |
| WO | 2005009954 A2 | 2/2005 |
| WO | 2005040109 A1 | 5/2005 |
| WO | 2005123687 A1 | 12/2005 |
| WO | 2006001958 A2 | 1/2006 |
| WO | 2006010629 A1 | 2/2006 |
| WO | 2006034446 A2 | 11/2006 |

OTHER PUBLICATIONS

DeBoer, Emergence of ghrelin as a treatment for cachexia syndromes, Nutrition (Sep. 2008).*

* cited by examiner

*Primary Examiner*—James O Wilson
*Assistant Examiner*—Erich A Leeser
(74) *Attorney, Agent, or Firm*—Bonnie L. Deppenbrock

(57) ABSTRACT

The present invention relates to compounds of formula (I)

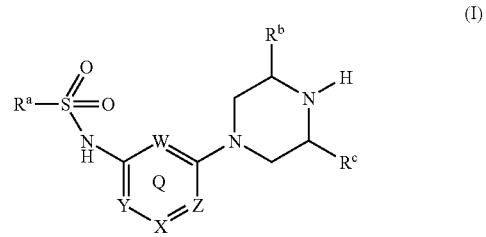

processes for their preparation, pharmaceutical compositions containing the same and to their use in the treatment of gastrointestinal and other disorders.

2 Claims, No Drawings

COMPOUNDS

CROSS-REFERENCE TO RELATED APPLICATIONS

This application claims the benefit of GB Application No. 0606526.2, filed Mar. 31, 2006 and GB Application No. 0704766.5, filed Mar. 12, 2007.

FIELD OF THE INVENTION

The present invention relates to novel piperazine derivatives, processes for their preparation, pharmaceutical compositions containing the same and to their use in the treatment of gastrointestinal and other disorders.

BACKGROUND OF THE INVENTION

Ghrelin is a 28 amino acid peptide predominantly produced by the stomach and to a lesser extent by the bowel, pancreas, kidney, placenta, pituitary and the arcuate nucleus of the hypothalamus. It has only recently been purified and isolated from the rat and human stomach (Kojima et al., Nature 1999; 402: 656), where it has been found in X/A endocrine cells associated with the acid-secreting parietal cells of the gastric glands. Studies have shown that ghrelin acts on growth hormone secretagogue receptors (GHS-R), stimulates the release of growth hormone, induces rat adiposity (Tschöp et al., Nature 2000, 407(6806), 908), controls gastric acid secretion (Masuda et al., Biochemical and Biophysical Research Communications 2000; 276: 905) and when released within the rodent arcuate nucleus (Kojima et al., Nature 1999; 402: 656; Lu et al., Neuroscience Letters. 2002; 321(3):157) or when administered i.c.v. (Nakazato et al., Nature 2001; 409: 194; Shintani et al., Diabetes 2001; 50: 227) stimulates an increase in food consumption. Systemically-administered ghrelin may also achieve the same, possibly by changing vagal nerve input to the brainstem vagal nuclei and hence, to the arcuate nucleus (Date et al., Gastroenterology 2002; 123: 1120). These studies indicate that GHS-R agonists have therapeutic utility in the treatment of different forms of cachexia and eating disorders.

Agonists of the ghrelin receptor have been described as useful in treating a growth hormone deficient state, stimulating an increase in food consumption thereby facilitating weight gain or maintenance of weight or appetite increase. This is particularly useful for a patient having a disease or disorder, or under going a treatment, that is accompanied by weight loss. Examples of diseases or disorders accompanied by weight loss include eating disorders (including anorexia, bulimia) cancer cachexia, AIDS, wasting, cachexia, and wasting in frail elderly. Examples of treatments accompanied by weight loss include chemotherapy, radiation therapy, temporary or permanent immobilization, and dialysis.

Further work with growth hormone secretagogues (e.g., WO 97/24369) suggests roles for ghrelin receptor agonists in the treatment or prevention of frailty associated with ageing, the acceleration of the repair of fractured bone, reducing protein catabolism after major surgery or during chronic illness, improving muscle strength and mobility control of congestive heart failure, and other metabolic disorders. Studies with such compounds also indicate a role in the promotion of sleep quality (WO 97/24369) and in the improvement of congestive heart failure after administration of ghrelin (Nagaya et al., J. Clin. Endocrinol. Metab. 2001, 86, 5854-5859; Circulation 2001, 104, 1430-1435).

In both anaesthetised and conscious rodents and in conscious dogs, ghrelin increases gastric motility and emptying (anaesthetised rat motility Masuda et al., Biochemical and Biophysical Research Communications 2000; 276: 905; rat gastric emptying Trudel et al., American Journal of Physiology 2002; 282: G948; mouse gastric emptying Asakawa et al., Gastroenterology 2001; 120: 337). This action can also be illustrated in vitro, by showing an ability of rat ghrelin to facilitate electrically-evoked, excitatory nerve-mediated contractions in rodent gastric fundus strips, a response mimicked by partial 5-$HT_4$ receptor agonists and indicative of a "prokinetic-like" response (Murray et al., British Journal of Pharmacology 2002; 136: 18P). Further, in conscious rats, i.c.v. administration of ghrelin reduces gastric acid secretion (Sibilia et al, Neuroendocrinology 2002; 75: 92); s.c. administration was without effect. Trudel and colleagues (American Journal of Physiology 2002; 282: G948) showed that ghrelin could reverse the gastric stasis created by invoking paralytic ileus via intestinal manipulation. Together, all of these data indicate that ghrelin might act as a gut hormone to facilitate both nutritional intake and digestion. This concurs with the proposal that the ability of ghrelin to evoke small reductions in pancreatic insulin secretion is consistent with the release of ghrelin during fasting conditions, when it will be important to maintain appropriate levels of blood sugars (see Muccioli et al., Eur J Pharmacology 2002, 440: 235).

Thus, in addition to conditions associated with cachexia (e.g. as a result of cancer), sarcopenia and/or those chronic diseases that may be exacerbated by loss of muscle mass (e.g. osteoporosis, rheumatoid arthritis, osteoarthritis, advancing age), growth hormone deficiency (e.g., when associated with age-related conditions), other disorders of metabolism, disorders in patterns of sleep or of congestive heart failure, GHS-R agonists will be useful treatments to alleviate symptoms associated with gastro-esophageal reflux and/or with dyspepsia, with or without appetite-/metabolic-related cachexia. Examples of such conditions include the reduction in feeding and the gastric stasis and emesis associated with anti-cancer treatment and other treatments or conditions which evoke similar symptoms, the gastroparesis associated with diabetes and gastroparesis and the symptoms associated with functional dyspepsia and gastro-esophageal reflux disease. Further, an ability to stimulate intestinal motility suggests that compounds active at ghrelin receptors will be useful treatments of paralytic ileus or pseudo-obstruction, and of conditions associated with constipation, such as constipation-predominant irritable bowel syndrome. An ability to reduce inflammation may also provide a use for compounds active at ghrelin receptors in the treatment of conditions such as gastritis and inflammatory bowel disease.

European patent application EP1159964 claims the use of compounds which stimulate the release of growth hormone as a means of stimulating the motility of the gastrointestinal system in a patient.

WO 95/06637 discloses a series of piperazine derivatives which are said to possess 5-$HT_{1D}$ receptor antagonist activity. WO 02/36562; WO 01/32660; WO 00/05225; WO 99/42465 and WO 98/27081 all disclose arylpiperazine sulfonamide derivatives that are claimed to be 5-$HT_6$ receptor antagonists. WO 02/74764; WO 02/74768; and WO 01/23374 all disclose dimethylpiperazine derivatives that are claimed to be selective 5$HT_{1B}$ receptor antagonists.

WO06/010629 discloses a series of arylpiperazine derivatives of formula (A):

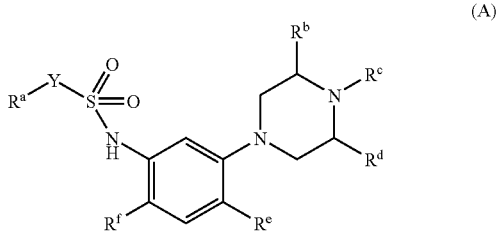

(A)

which are said to possess agonistic activity at the growth hormone secretagogue (GHS) receptors.

SUMMARY OF THE INVENTION

We have now found a novel class of arylpiperazine sulfonamide derivatives which exhibit a selective agonistic activity at the growth hormone secretagogue (GHS) receptors.

The present invention therefore provides a compound of formula (I) or a pharmaceutically acceptable derivative thereof:

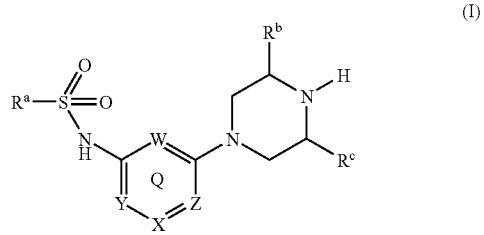

(I)

in which $R^a$ is optionally substituted aryl or optionally substituted heteroaryl;

$R^b$ and $R^c$ are independently hydrogen or $C_{1-6}$alkyl;

Q is a ring wherein W and X are independently CH or N and Y and Z are independently $CR^d$ or N; and when present $R^d$ is independently selected from the group consisting of hydrogen, $C_{1-6}$alkyl, $C_{1-6}$alkoxy, halogen, hydroxyl, trifluoromethyl, $C_{1-6}$haloalkoxy, oxo and cyano; wherein at least one of $R^b$ and $R^c$ is $C_{1-6}$alkyl and at least one of W, X, Y and Z is N.

DETAILED DESCRIPTION

Alkyl groups, whether alone or as part of another group, may be straight chain or branched. The term "halogen" is used herein to describe, unless otherwise stated, a group selected from fluorine, chlorine, bromine or iodine.

The term "aryl" as a group or part of a group includes phenyl and naphthyl. Where used herein the term naphthyl is intended, unless otherwise stated, to denote both naphth-1-yl and naphth-2-yl groups.

The term "heteroaryl" is intended to mean a 5-6 membered monocyclic aromatic or a fused 8-11 membered bicyclic aromatic ring containing heteroatoms selected from oxygen, nitrogen and sulphur.

When the term heteroaryl represents a 5 or 6 membered group it contains a heteroatom selected from O, N or S and may optionally contain a further 1 to 3 nitrogen atoms. When heteroaryl represents a 6-membered group it contains from 1 to 3 nitrogen atoms.

When the term heteroaryl represents a fused 8-11 membered bicyclic aromatic ring it contains 1 to 3 heteroatoms selected from O, N or S.

Suitable examples of such monocyclic aromatic rings include thienyl, furanyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. The term a fused 8-11 membered bicyclic aromatic group includes groups wherein one of the rings is partially saturated.

Suitable examples of such fused aromatic rings include benzofused heterocyclic rings such as quinolinyl, isoquinolinyl, quinazolinyl, quinoxalinyl, cinnolinyl, naphthyridinyl, indolyl, indazolyl, pyrrolopyridinyl, thienopyridyl, benzofuranyl, benzothienyl, benzimidazolyl, benzoxazolyl, benzisoxazolyl, benzothiazolyl, benzisothiazolyl, benzoxadiazolyl, benzothiadiazolyl, benzodioxanyl, indolinyl, isoindolinyl, tetrahydroquinolinyl, tetrahydroisoquinolinyl, benzazepinyl or chromanyl.

The aryl and heteroaryl groups according to the definitions above included such groups wherein they may be optionally substituted by one to three substituents which may be the same or different, and which are selected from the group consisting of halogen, hydroxy, cyano, nitro, oxo, trifluoromethyl, trifluoromethoxy, fluoromethoxy, difluoromethoxy, $C_{1-6}$ alkyl, $C_{3-6}$ cycloalkyl, pentafluoroethyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, arylsulfonyl, arylsulfonyloxy, arylsulfonyl$C_{1-6}$ alkyl, aryloxy, heteroaryloxy, aroyl, aroyl$C_{1-6}$ alkyl, aryl$C_{1-6}$ alkanoyl, aryl, heteroaryl, heterocyclyl, or a group $NR^1R^2$, $CONR^1R^2$, $SO_2NR^1R^2$, $NR^1COR^2$ or $NR^1SO_2R^2$ wherein $R^1$ and $R^2$ independently represent hydrogen, $C_{1-6}$ alkyl, $C_{3-7}$ cycloalkyl, aryl, or heteroaryl, or together with the nitrogen atom form a 5- to 7-membered non-aromatic heterocyclic ring which may optionally contain an additional ring member selected from O, S or N.

Suitable $C_{3-6}$cycloalkyl groups include cyclopropyl, cyclobutyl, cyclopentyl and cyclohexyl.

When $R^a$ is substituted by aryl or heteroaryl groups these substituents are optionally further substituted provided that the further substituents are not aryl or heteroaryl. Further substituents on such aryl and heteroaryl groups may for example be selected from halogen, cyano, $C_{1-6}$alkyl, $C_{1-6}$ alkoxy and oxo. Particularly chloro, cyano, methyl, and oxo. In another aspect, substituents on such aryl and heteroaryl groups may for example be selected from fluoro, methoxy and methoxymethyl.

The term "heterocyclyl" is intended to mean a 4-7 membered monocyclic saturated or partially unsaturated aliphatic ring containing 1 to 3 heteroatoms selected from oxygen, sulphur or nitrogen. Suitable examples of such monocyclic rings include pyrrolidinyl, piperidinyl, piperazinyl, morpholinyl, thiomorpholinyl, diazepanyl, azepanyl, and tetrahydrofuranyl.

One suitable group of compounds of this invention are of formula (IA): wherein

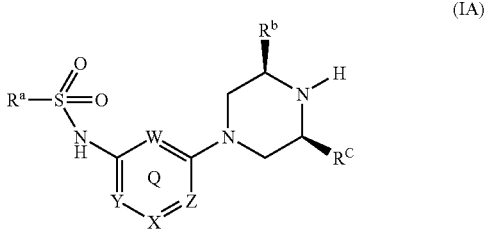

(IA)

$R^a$, Q, $R^b$, $R^c$, $R^d$, W, X, Y and Z are as defined for formula (I).

In a suitable group of compounds of formulae (I) and (IA):
$R^a$ is optionally substituted phenyl; and/or
$R^b$ and $R^c$ are both methyl; and/or
Q is selected from the group consisting of 2-pyridyl, 3-pyridyl, 4-pyridinyl and 4-pyrimidinyl; and/or
each $R^d$ is hydrogen or methoxy.

Suitably $R^a$ may be substituted by optionally substituted furanyl or optionally substituted thienyl.

Specific examples of formula (I) are:

N-{6-[cis-3,5-Dimethyl-1-piperazinyl]-2-pyridinyl}-3-fluoro-4-(5-methyl-2-furanyl)benzenesulfonamide;

N-(2-[cis-3,5-Dimethyl-1-piperazinyl]-4-pyridinyl)-4-(5-methyl-2-furanyl)benzenesulfonamide;

N-[6-[cis-3,5-Dimethyl-1-piperazinyl]-3-(methyloxy)-2-pyridinyl]-3-fluoro-4-(5-methyl-2-furanyl)benzenesulfonamide;

N-(2-[cis-3,5-Dimethyl-1-piperazinyl]-4-pyrimidinyl)-3-fluoro-4-(5-methyl-2-furanyl)benzenesulfonamide;

2-Chloro-N-[6-[(3R,5S)-3,5-dimethyl-1-piperazinyl]-3-(methyloxy)-2-pyridinyl]-4-(5-methyl-2-furanyl)benzenesulfonamide 2-Chloro-N-[6-[(3R,5S)-3,5-dimethyl-1-piperazinyl]-3-(methyloxy)-2-pyridinyl]-4-(4-methyl-2-thienyl)benzenesulfonamide 2-Chloro-N-[6-[(3R,5S)-3,5-dimethyl-1-piperazinyl]-3-(methyloxy)-2-pyridinyl]-4-(3-furanyl)benzenesulfonamide 2-Chloro-N-[6-[(3R,5S)-3,5-dimethyl-1-piperazinyl]-3-(methyloxy)-2-pyridinyl]-4-(5-methyl-2-thienyl)benzenesulfonamide N-[6-[(3R,5S)-3,5-dimethyl-1-piperazinyl]-3-(methyloxy)-2-pyridinyl]-4-(5-methyl-2-furanyl)benzenesulfonamide N-[6-[(3R,5S)-3,5-Dimethyl-1-piperazinyl]-3-(methyloxy)-2-pyridinyl]-2'-fluoro-5'-(methyloxy)-4-biphenylsulfonamide N-[6-[(3R,5S)-3,5-Dimethyl-1-piperazinyl]-3-(methyloxy)-2-pyridinyl]-2-fluoro-4-(5-methyl-2-furanyl)benzenesulfonamide N-{4-[(3R,5S)-3,5-Dimethyl-1-piperazinyl]-2-pyridinyl}-3-fluoro-4-(5-methyl-2-furanyl)benzenesulfonamide N-[5-[cis-3,5-Dimethyl-1-piperazinyl]-2-(methyloxy)-3-pyridinyl]-3-fluoro-4-(5-methyl-2-furanyl)benzenesulfonamide N-{5-[cis-3,5-Dimethyl-1-piperazinyl]-3-pyridinyl}-3-fluoro-4-(5-methyl-2-furanyl)benzenesulfonamide N-{5-[cis-3,5-Dimethyl-1-piperazinyl]-2-oxo-1,2-dihydro-3-pyridinyl}-3-fluoro-4-(5-methyl-2-furanyl)benzenesulfonamide Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolic or residue thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic, salicylic, lactic, mandelic or naphthalenesulfonic acid.

The compounds of formula (I) and their derivatives may be prepared in crystalline or non-crystalline form, and, if crystalline, may optionally be hydrated or solvated. This invention includes within its scope stoichiometric hydrates as well as compounds containing variable amounts of water.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Compounds of the invention may be prepared using procedures which are analogous to those known in the art. However, the present invention also provides processes for the preparation of a compound of formula (I) or pharmaceutically acceptable derivatives thereof, comprising:

Process (a) Coupling of a compound of formula (II)

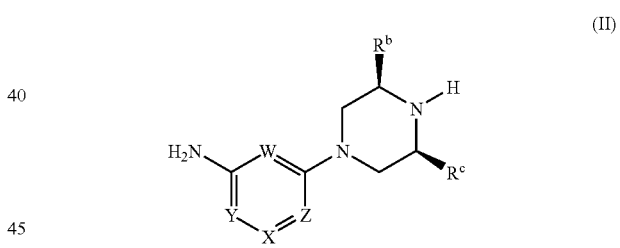

(II)

wherein W, X, Y, Z, $R^b$ and $R^c$ are as defined in formula (I) or protected derivatives thereof, with a compound of formula (III) wherein $R^a$ is as defined in formula (I) and L1 is a suitable leaving group, such as a suitable halogen group (e.g. chlorine) or a pentafluorophenyloxy group.

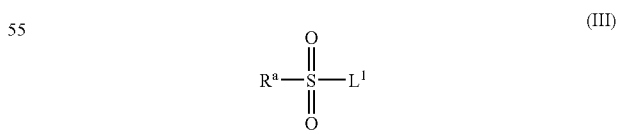

(III)

Process (a) typically comprises the use of a base, such as pyridine. Process (a) may comprise the use of a base, such as pyridine in an appropriate solvent such as dichloromethane at an appropriate temperature, such as room temperature or 80° C. Alternatively, process (a) may comprise the use of a base such as pyridine in an appropriate solvent such as dichloromethane, to form the bis-sulfonamide, which can then be cleaved to the mono-sulfonamide with an appropriate base such as aqueous sodium hydroxide as an appropriate temperature such as 40° C.

Compounds of formulae (III) are commercially available or may be prepared according to known methods or analogous to known methods.

Or Process (b) Interconversion of compounds of formula (I) to other compounds of formula (I).

Process (b) may be performed using conventional transition metal mediated coupling reactions. Examples of transition metal mediated coupling reactions useful as interconversion procedures include the following: palladium catalysed coupling reactions between organic electrophiles, such as aryl halides, and organometallic reagents, for example stannanes (Stille cross-coupling reactions) or other suitable reagents, for example boronic acids (Suzuki cross-coupling reactions); and copper mediated coupling reactions between phenols and boronic acids.

Compounds of formula (II) may be prepared in accordance with the following scheme:

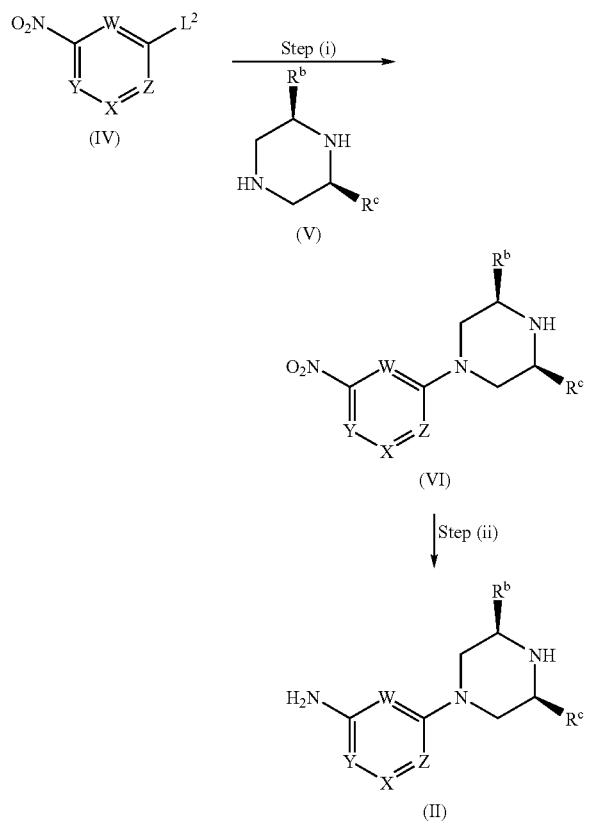

wherein W, X, Y, Z, $R^b$ and $R^c$ are defined as above, $L^2$ is a suitable leaving group, such as halogen (e.g. bromine).

When the leaving group $L^2$ is a halogen atom such (e.g. bromine or chlorine), step (i) typically comprises of treatment of a compound of formula (IV) with a piperazine of formula (V) with a transition metal catalyst such as a palladium salt (e.g. tris(dibenzylideneacetone)dipalladium(0)) in combination with a suitable ligand (e.g. 2-dicyclohexylphosphino-2'-(N,N-dimethylamino)biphenyl) in the presence of a base such as sodium tert-butoxide in an appropriate solvent such as dioxane at an appropriate temperature (e.g. reflux). The reaction may also be carried out in a microwave reactor in an appropriate solvent such as dioxane at an appropriate temperature (e.g. 120° C.).

Step (ii) comprises the reduction of the nitro group in a compound of formula (VI) to an aniline of formula (II). Step (ii) may typically be performed under transition metal catalysed hydrogenation conditions, for example, under an atmosphere of hydrogen employing a suitable catalyst, such as palladium on charcoal, in a suitable solvent, such as ethanol or using tin (II) chloride in an appropriate solvent such as ethanol at an appropriate temperature (e.g. reflux).

Compounds of formulae (IV) and (V) are commercially available or may be prepared according to known methods or by analogy to known methods.

Or Process (c) Reacting a compound of formula (VII)

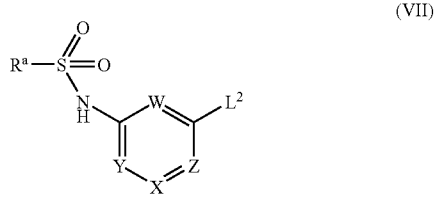

wherein W, X, Y, Z and $R^a$ are defined as above and $L^2$ is a suitable leaving group, such as halogen (e.g. iodine, bromine or chlorine), with a piperazine compound of formula (V) to give a compound of formula (I).

Process (c) may typically be performed with a transition metal catalyst such as a palladium salt (e.g. tris(dibenzylideneacetone)dipalladium(0)) in combination with a suitable ligand (e.g. 2-dicyclohexylphosphino-2'-(N,N-dimethylamino)biphenyl) in the presence of a base such as sodium tert-butoxide in an appropriate solvent such as dioxane at an appropriate temperature such as reflux. The reaction may also be carried out in a microwave reactor in an appropriate solvent such as dioxane at an appropriate temperature such as 120° C. Process (c) may also comprise the reaction of a compound of formula (VII) with a piperazine of formula (V) in an appropriate solvent such as 1-methyl-2-pyrrolidinone or pyridine at an appropriate temperature such as 100-200° C. (e.g. in a microwave reactor).

Compounds of formula (VII) may be interconverted to other compounds of formula (VII).

Compounds of formula (VII) may be prepared from an aniline of formula (VIII) and compound of formula (III) in an analogous manner to that described in process (a)

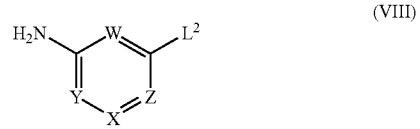

wherein W, X, Y and Z are defined as above and $L^2$ is a suitable leaving group, such as halogen (e.g. iodine, bromine or chlorine).

Anilines of formula (VIII) are commercially available or may be prepared according to known methods or analogous to known methods. For example compounds of formula (VIII) may be prepared by displacement of a chloro compound of formula (IX) using aqueous ammonia in an appropriate solvent such as ethanol.

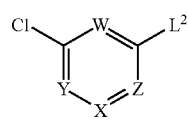

(IX)

wherein W, X, Y and Z are defined as above and $L^2$ is a suitable leaving group, such as halogen (e.g. iodine, bromine or chlorine).

Those skilled in the art will appreciate that it may be necessary to protect certain groups. Suitable protecting groups and methods for their attachment and removal are conventional in the art of organic chemistry, such as those described in T. W. Greene "Protective Groups in Organic Synthesis" (J. Wiley and Son, 1991). For example, suitable protecting groups for the piperazine group include t-butyloxycarbonyl, benzyl, trifluoroacetyl, benzyloxycarbonyl, 2',2',2'-trichloroethoxycarbonyl, and methyl the latter of which may be removed with 1-chloroethyl chloroformate according to standard procedures.

The compounds of formula (I) have been found to be GHS-R agonists in the GTPγS and FLIPR (Fluorometric Light Imaging Plate Reader) assay described herein.

Compounds of formula (I) and their pharmaceutically acceptable derivatives (hereinafter "compounds of the invention") are therefore of use in the treatment of conditions or disorders which are mediated by compounds acting at the growth hormone secretagogue (GHS) receptors. In particular the compounds of the invention are of use in the treatment of cachexia, sarcopenia, osteoporosis, rheumatoid arthritis, osteoarthritis, frailty associated with aging, growth hormone deficiency, metabolic disorders, sleep disorders, Alzheimer's Disease, congestive heart failure, alleviation of symptoms associated with gastro-esophageal reflux and/or with dyspepsia, with or without appetite-/metabolic-related cachexia, emesis, gastritis, inflammatory bowel disease, decreased gastric motility during procedures such as enteral feeding, the treatments of paralytic ileus or pseudo-obstruction, and of conditions associated with constipation, such as constipation-predominant irritable bowel syndrome.

It is to be understood that "treatment" as used herein includes prophylaxis as well as alleviation of established symptoms.

Thus the invention also provides a compound of the invention or pharmaceutically acceptable derivatives thereof, for use as a therapeutic substance, in particular in the treatment of the conditions/disorders which can be mediated via the GHS receptors. In particular the invention provides a compound of the invention or a pharmaceutically acceptable derivative thereof for use as a therapeutic substance in the treatment of cachexia, sarcopenia, osteoporosis, rheumatoid arthritis, osteoarthritis, frailty associated with aging, growth hormone deficiency, metabolic disorders, sleep disorders, Alzheimer's Disease, congestive heart failure, alleviation of symptoms associated with gastro-esophageal reflux and/or with dyspepsia, with or without appetite-/metabolic-related cachexia, emesis, gastritis, inflammatory bowel disease, decreased gastric motility during procedures such as enteral feeding, the treatments of paralytic ileus or pseudo-obstruction, and of conditions associated with constipation, such as constipation-predominant irritable bowel syndrome. It is to be understood that compounds of the invention may also be used in combination with other therapeutic substances.

The invention further provides a method of treatment of conditions or disorders in mammals including humans which can be mediated via the GHS receptors, which comprises administering to the sufferer a therapeutically safe and effective amount of a compound of the invention.

In another aspect, the invention provides for the use of a compound of the invention in the manufacture of a medicament for use in the treatment of the conditions or disorders mediated via the GHS receptors.

In order to use the compounds of the invention in therapy, they will normally be formulated into a pharmaceutical composition in accordance with standard pharmaceutical practice. The present invention also provides a pharmaceutical composition, which comprises a compound of the invention, and a pharmaceutically acceptable carrier or excipient.

In a further aspect, the present invention provides a process for preparing a pharmaceutical composition, the process comprising mixing a compound of the invention and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable derivatives thereof and a sterile vehicle. Formulations for injection may be presented in unit dosage form e.g. in ampoules or in multi-dose, utilising a compound of the invention or pharmaceutically acceptable derivatives thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of the invention may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

No toxicological effects are indicated/expected when a compound (of the invention) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following descriptions and Examples illustrate the preparation of compounds of the invention. Each Example was characterised and assayed either as the free base or hydrochloride salt or occasionally as the formic acid salt directly from mass directed autoprep HPLC. The hydrochloride salts were prepared by dissolving the pure material in dichloromethane or methanol and acidifying with ethereal HCl.

Where so indicated in the experimental section microwave heating was performed in Biotage Initiator 60 or Personal Chemistry Optimiser instruments. These instruments allowed the control of temperature up to 250° C. and allowed pressures up to 20 bar with microwave radiation up to 300 W at 2.45 GHz.

Conditions, Hardware and Software Used for Mass Directed Auto-Purification System Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Detector
Waters ZQ Mass Spectrometer
Gilson 202 fraction collector
Gilson Aspec waste collector Software
Waters Masslynx version 4 SP2

Column
The columns used are Waters Atlantis, the dimensions of which are 19 mm×100 mm (small scale) and 30 mm×100 mm (large scale). The stationary phase particle size is 5 μm.

Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol Methods
There are four methods used depending on the analytical retention time of the compound of interest. They all have a 13.5-minute runtime, which comprises of a 10-minute gradient followed by a 13.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 mins)

Flow Rate
All of the above methods have a flow rate of either 20 mls/min (Small Scale) or 40 mls/min (Large Scale)

Conditions, Hardware and Software for Analytical LCMS Systems

Hardware
Agilent 1100 Gradient Pump
Agilent 1100 Autosampler
Agilent 1100 DAD Detector Agilent 1100 Degasser
Agilent 1100 Oven
Agilent 1100 Controller
Waters ZQ Mass Spectrometer
Sedere Sedex 55, Sedere Sedex 85 or Polymer Labs PL-ELS-2100

Software
Waters MassLynx version 4.0 SP2

Column
The column used is a Waters Atlantis, the dimensions of which are 4.6 mm×50 mm. The stationary phase particle size is 3 µm.

Solvents
A: Aqueous solvent=Water+0.05% Formic Acid
B: Organic solvent=Acetonitrile+0.05% Formic Acid Method
The generic method used has a 5 minute runtime.

| Time/min | % B |
| --- | --- |
| 0 | 3 |
| 0.1 | 3 |
| 4 | 97 |
| 4.8 | 97 |
| 4.9 | 3 |
| 5.0 | 3 |

Flow Rate
The above method has a flow rate of 3 ml/mins

Conditions Used for NMR

Hardware
Bruker 400 MHz Ultrashield
Bruker B-ACS60 Autosampler
Bruker Advance 400 Console
Bruker DPX250
Bruker AVANCE 500
Bruker DRX600

Software
User interface—NMR Kiosk
Controlling software—XWin NMR version 3.0

EXAMPLES

Description 1: 4-Bromo-N-(6-bromo-2-pyridinyl)-3-fluorobenzenesulfonamide (D1)

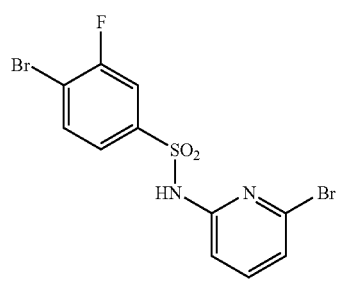

A solution of 4-bromo-3-fluorobenzenesulfonyl chloride (684 mg, 370 µl, 2.5 mmol) in dichloromethane (2 ml) was added slowly at room temperature to a solution of 2-amino-6-bromopyridine (346 mg, 2.0 mmol) in pyridine (2 ml). The reaction mixture was stirred at room temperature for 1 h. The solvent was evaporated and the residue partitioned between ethyl acetate (50 ml) and water (50 ml). The organic phase washed with water (×2), separated, dried and evaporated. Purification by column chromatography eluting with 20-60% ethyl acetate in hexanes afforded the title compound (D1), MS (ES⁺) m/e 409, 411, 413 [M+H]⁺.

Description 2: 4-Bromo-N-(6-[cis-3,5-dimethyl-1-piperazinyl]-2-pyridinyl)-3-fluorobenzenesulfonamide (D2)

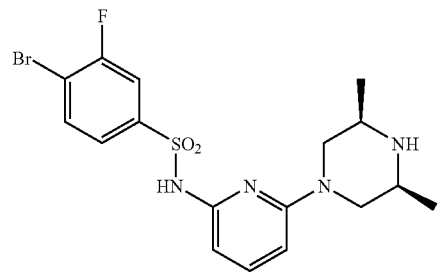

A solution of 4-bromo-N-(6-bromo-2-pyridinyl)-3-fluorobenzenesulfonamide (D1) (300 mg, 0.73 mmol) and cis-2,6-dimethylpiperazine (600 mg, 5.4 mmol) in 1-methyl-2-pyrrolidinone (5 ml) and water (0.5 ml) was microwaved at 200° C. for 2000 sec. The reaction mixture was diluted with ethyl acetate (20 ml) and washed with water (3×10 ml). The organic phase was dried and evaporated. Purification by column chromatography eluting with 5% methanol in dichloromethane afforded the title compound (D2), MS (ES⁺) m/e 443, 445 [M+H]⁺.

Description 3:
4-Bromo-N-(2-chloro-4-pyridinyl)benzenesulfonamide (D3)

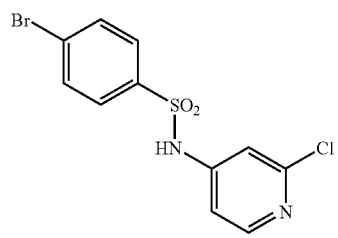

4-Bromobenzenesulfonyl chloride (3.19 g, 12.5 mmol) was added to a solution of 4-amino-2-chloropyridine (642 mg, 5 mmol) in pyridine (5 ml) and dichloromethane (5 ml). The reaction mixture was stirred at room temperature for 2 h. The solvent was evaporated and the residue suspended in 2M NaOH (25 ml) and heated at 60° C. for 1 h. The reaction mixture was extracted with ethyl acetate (2×25 ml). The extracts were washed, dried and evaporated. The residue was suspended in methanol and filtered. Evaporation of the filtrate and trituration with diethyl ether afforded the title compound (D3), ¹H NMR (DMSO) δ: 6.54 (1H, d), 6.62 (1H, s), 7.60-7.63 (4H, m), 7.66 (1H, d).

Description 4: N-(2-Chloro-4-pyridinyl)-4-(5-methyl-2-furanyl)benzenesulfonamide (D4)

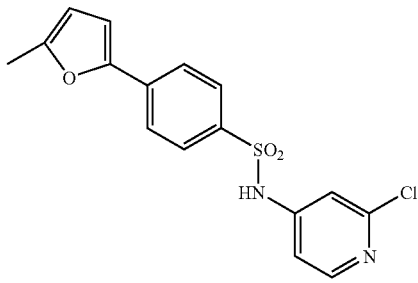

A mixture of 4-chloro-N-(2-chloro-4-pyridinyl)benzenesulfonamide (D3) (350 mg, 1 mmol), 5-methylfuran-2-boronic acid (150 mg, 1.2 mmol), sodium carbonate (230 mg, 2.2 mmol) and dichlorobis(triphenylphosphine) palladium(0) (20 mg, 15 mol %) in 1,2-dimethoxyethane (3 ml) and water (1 ml) was microwaved at 120° C. for 20 min. The reaction mixture was partitioned between ethyl acetate (5 ml) and water (5 ml) and the organic phase was dried and evaporated. Purification by column chromatography eluting with 5-50% ethyl acetate in hexanes afforded the title compound (D4), MS (ES$^+$) m/e 349, 351 [M+H]$^+$.

Description 5: 6-Bromo-3-(methyloxy)-2-nitropyridine (D5)

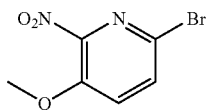

Method A

A mixture of 6-bromo-3-hydroxy-2-nitropyridine (9.4 g, 42.8 mmol) and potassium carbonate (6.9 g, 50 mmol) in acetone (100 ml) was treated with iodomethane (7.1 g, 3.11 ml, 50 mmol) and stirred at 40° C. After 2, 4, 6 and 8 hours further portions of iodomethane (7.1 g, 3.11 ml, 50 mmol) were added. After 36 h the solvent was evaporated and the residue was partitioned between ethyl acetate and water. The organic phase washed with water, dried and evaporated. Purification by column chromatography eluting with 5-50% ethyl acetate in hexanes afforded the title compound (D5), MS (ES$^+$) m/e 233, 235 [M+H]$^+$.

Method B

N,N-Dimethylformamide (DMF)(700 mL) was added to a stirred mixture of 6-bromo-3-hydroxy-2-nitropyridine (70.9 g, 324 mmol) and cesium carbonate (211 g, 648 mmol) under argon at ambient temperature, resulting in a rise to 30° C. The stirred mixture was cooled to 10° C. and iodomethane (41 ml, 659 mmol) was added in one portion. The cooling bath was removed and the mixture was stirred at room temperature overnight under argon. The DMF was evaporated in vacuo and to the residue was added water (1 L). This mixture was extracted with ethyl acetate (3×500 ml) and the combined extracts were successively washed with 2M sodium hydroxide (400 mL), water (400 mL), water (800 mL) containing saturated brine (25 mL) and saturated brine (800 mL). The organic solution was dried (MgSO$_4$) and evaporated to give a tanned solid. (52.8 g)

Two further batches of D5 (yielding 54.2 g and 52.1 g) were prepared in a similar manner to that described above from 6-bromo-3-hydroxy-2-nitropyridine.

129 g of material from the combined batches was purified by dissolving in dichloromethane and filtering from some insoluble material. The filtrate was applied to a Flash 150 Biotage silica gel chromatography column and eluted with a 30%-60% increasing gradient of dichloromethane/hexane. Product fractions were pooled and evaporated to give the title compound (D5) as a pale yellow solid (98.1 g).

$\delta$H(CDCl$_3$, 400 MHz) 3.99 (3H, s), 7.43 (1H, d, J=8.4 Hz), 7.69 (1H, d, J=8.4 Hz).

Method C

6-Bromo-2-nitro-3-pyridinol (23.11 g, 106 mmol) and potassium carbonate (43.95 g, 318 mmol) were suspended in acetone (500 mL). Methyl iodide (7.92 ml, 127 mmol) was added and the mixture heated at 50° C. for 4 hours. Further methyl iodide (2 ml, 31.8 mmol) was added and heated for 2 hours. A further portion of methyl iodide (3.3 ml, 53 mmol) was added and the mixture heated at 50° C. overnight. The reaction mixture was cooled, filtered and the solids washed with acetone. The filtrate was concentrated in vacuo. And the residue was triturated with chloroform, the solids filtered and the filtrate concentrated in vacuo. The residue was purified by flash chromatography (Biotage Horizon, 65, 0-100% ethyl acetate/hexane) to afford the title product (D5): 7.89 g. MS (ES$^+$) m/e 233/235 [M+H]$^+$.

Method D

A mixture of 6-bromo-3-hydroxy-2-nitropyridine (44.81 g, 0.214 mol), and potassium carbonate (74.17 g, 0.537 mol) in acetone (750 mL) was treated with iodomethane (15.99 ml, 0.256 mmol) and stirred at 50° C. Two further additions of 1.2 equivalents of iodomethane were made over a period of approximately four hours. The solvent was filtered, evaporated, and the residue dissolved in ethyl acetate (500 mL) and washed with water (300 mL), saturated sodium hydrogen carbonate solution (300 mL), water (300 mL) and brine (300 mL). The organic layer was dried (MgSO$_4$) and evaporated. Purification by column chromatography eluting with 0-100% ethyl acetate in hexane gave the title compound as a cream coloured solid (D5) (10.47 g) MS (ES$^+$) m/e 233, 235 [M+H]$^+$.

Description 6: cis-3,5-Dimethyl-1-[5-(methyloxy)-6-nitro-2-pyridinyl]piperazine (D6)

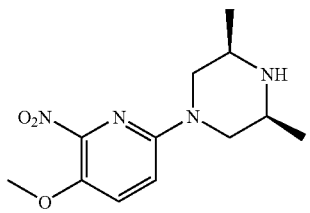

Method A1

A mixture of 6-bromo-3-(methyloxy)-2-nitropyridine (D5, Method A) (1.5 g, 6.4 mmol), cis-2,6-dimethylpiperazine (880 mg, 7.7 mmol), sodium tert-butoxide (1.24 g, 12.9 mmol), tris(dibenzylideneacetone)dipalladium(0) (294 mg, 5 mol %), and 2-dicyclohexylphosphino-2'-(N,N-dimethylamino)biphenyl (300 mg, 10 mol %) in dioxan (20 ml) was heated at 110° C. overnight. The reaction mixture was diluted with ethyl acetate and filtered through celite. The filtrate was evaporated and the residue purified by column chromatography eluting with 5% methanol in dichloromethane followed by reverse phase silica gel chromatography eluting with 5-100% acetonitrile in water to afford the title compound (D6), MS (ES+) m/e 267 [M+H]+.

Method A2

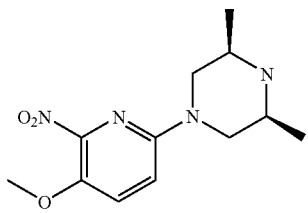

A mixture of 6-bromo3-(methyloxy)-2-nitropyridine(D5, Method A) (1.0 g, 4.3 mmol), cis-2,6-dimethylpiperazine (980 mg, 8.6 mmol), sodium tert-butoxide (825 mg, 8.6 mmol), tris(dibenzylideneacetone)dipalladium(0) (196 mg, 5 mol %) and 20dicyclohexylphosphino-2'-(N,N-dimethylamino)biphenyl(168 mg, 10 mol %) in dioxan (20 ml) was heated at 110° C. overnight. The cooled reaction mixture was diluted with ethyl acetate (20 ml) and extracted with 1M hydrochloric acid. The extracts were basified with 50% aqueous sodium hydroxide then extracted with ethyl acetate. The organic extracts were dried and evaporated. Purification by column chromatography eluting with 5% methanol in dichloromethane gave the title compound (D6). MS (ES+) m/e 267 [M+H]+.

Method B

6-Bromo-3-(methyloxy)-2-nitropyridine (D5, Method B) (45.0 g, 193 mmol) was dissolved in dioxane (1.5 L) and cooled to 14° C. under argon. Cis-2,6-dimethylpiperazine (44.1 g, 386 mmol) was added in one portion and after 15 minutes, when all the materials had dissolved, 2-dicyclohexylphosphino-2'-(N,N-dimethylamino)biphenyl (11.3 g, 15 mol %) was added followed, 2 mins later, by the addition of tris(dibenzylideneacetone)dipalladium(0) (17.6 g, 10 mol %). After 10 mins stirring at 14° C., under argon, sodium tert-butoxide (22.3 g, 231 mmol) was then added over 35 mins maintaining the reaction temperature at approx 14° C., under argon. The reaction was stirred at 14° C. for 3.5 hours (monitored by LCMS) and then water (1 L) and glacial acetic acid (16.5 mL) were added with stirring. To the mixture was then added a saturated solution of sodium hydrogen carbonate (500 ml) and ethyl acetate (1.1 L) and the mixture was vigorously shaken in a separating funnel. The layers were separated and the organic phase washed with 5% brine (2×1 L). The combined aqueous extracts were re-extracted with ethyl acetate (2×500 mL). The combined organic extracts were dried (Mg SO4) and filtered through Kieselghur. The filtrate was concentrated in vacuo to give the crude title compound as a red oil.

Another batch of this crude material was prepared from 6-bromo-3-(methyloxy)-2-nitropyridine (D5) (49.0 g, 210 mmol) in a similar manner to that described above.

The combined crude materials from both batches were then purified by chromatography [silica gel, eluting firstly with a 50%-100% increasing ethyl acetate/hexane gradient and then with a 3%-15% increasing 2M ammonia in methanol/ethyl acetate gradient]. Product fractions were pooled and evaporated to afford the title compound as a red oily solid (D6)(62.2 g, 234 mmol, 58%), MS (ES+) m/e 267 [M+H]+.

A further purified batch of the title compound (3.2 g) was prepared in a similar way to that described above.

Method C

6-Bromo-3-(methyloxy)-2-nitropyridine (D5, Method C) (6.99 g. 30 mmol) was dissolved in dioxane (150 mL). Tris (dibenzylideneacetone)dipalladium(0) (1.38 g, 1.5 mmol) and 2-dicyclohexylphosphino-2'-(N,N-dimethylamino)biphenyl (1.18 g, 3 mmol) were added. Sodium tert-butoxide (5.77 g, 60 mmol) then cis-2,6-dimethylpiperazine (5.14 g, 45 mmol) were added and the mixture stirred at room temperature for 5 hours. The mixture was filtered through celite, washed with ethyl acetate and the filtrate concentrated in vacuo. The residue was partitioned between ethyl acetate and water. The organic phase was washed with 50% brine (×3), brine, dried over anhydrous sodium sulphate and concentrated in vacuo. The residue was purified by flash chromatography, (Biotage SP4, 40+M, 0-20% 2M ammonia/methanol in dichloromethane afford the title product (D6): 3.13 g, MS (ES+) m/e 267 [M+H]+.

Method D

6-Bromo-3-(methyloxy)-2-nitropyridine (D5, Method D) (8.0 g, 34.1 mmol) was dissolved in dioxane (300 mL) and cooled to 13° C. Cis-2,6-dimethylpiperazine (7.79 g, 68.3 mmol), 2-dicyclohexylphosphino-2'-(N,N-dimethylamino) biphenyl (2.013 g, 15 mol %) and tris(dibenzylideneacetone) dipalladium(0) (3.121 g, 10 mol %) were added. Sodium tert-butoxide (6.55 g, 68.3 mmol) was then added over 1 minute with the temperature maintained below 15° C. The reaction was stirred at <18° C. for 5.5 hours (monitored by LCMS) and the water (25 mL) was added and the reaction filtered through cealite and filtrate evaporated to give a dark red semi-solid which was dissolved in ethyl acetate (600 mL) and washed with saturated sodium hydrogen carbonate (3×300 mL) and brine (30 mL). The organic layer was dried (MgSO4) and evaporated to give a red solid which was purified by chromatography [silica gel, eluting with 0 to 20% (2M ammonia/methanol)/Ethyl acetate]. Product fractions were evaporated to afford the title compound as a red solid (D6), MS (ES+) m/e 267 [M+H]+.

Description 7: 6-[cis-3,5-Dimethyl-1-piperazinyl]-3-(methyloxy)-2-pyridinamine (D7)

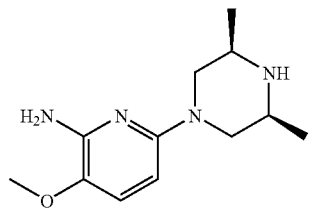

Method A

Tin (II) chloride dihydrate (550 mg, 2.4 mmol) was added to a solution of cis-3,5-dimethyl-1-[5-(methyloxy)-6-nitro-2-pyridinyl]piperazine (D6, Method A2) (320 mg, 1.2 mmol) in ethanol (20 ml) and heated at 80° C. for 2 h. The reaction mixture was cooled to room temperature and solvent was evaporated and the residue diluted with water (20 ml). The mixture was basified by the portion-wise addition of solid potassium carbonate. The mixture was extracted with ethyl acetate (×2). The combined organic phases were dried and evaporated to afford the title compound, (D7) MS (ES+) m/e 237 [M+H]+.

Method B

A solution of (3R,5S)-3,5-dimethyl-1-[5-(methyloxy)-6-nitro-2-pyridinyl]piperazine (D6, Method B) (62.3 g, 234 mmol) in methanol (1.8 L) was poured onto a slurry of 10% palladium on carbon (9.3 g) in water (30 mL). Total transfer of compound D6 was ensured using a further quantity of methanol (100 mL). The suspension was stirred for 6 h under an atmosphere of hydrogen (15-18 psi) at between ambient temperature and 30° C. The reaction mixture was then filtered through Kieselghur, washing the latter with methanol (2×200 mL), and the filtrate and washings were evaporated to give a dark brown oil (55.7 g). This material was purified by chromatography [silica gel, eluting with 0%-25% increasing gradient of methanol/dichloromethane]. Product fractions were pooled and evaporated to afford the title compound as a dark brown oil (D7) (40 g, 169 mmol, 72%), MS (ES$^+$) m/e 237 [M+H]$^+$.

Method C

Cis-3,5-dimethyl-1-[5-(methyloxy)-6-nitro-2-pyridinyl]piperazine (D6, Method C) (3.13 g, 12 mmol) was hydrogenated at room temperature at 1 atmosphere of hydrogen over 10% palladium/charcoal paste (300 mg) in methanol (100 mL) for 5 hours. The catalyst was filtered and the filtrate concentrated in vacuo to afford the title product (D7), 3.40 g, MS (ES$^+$) m/e 237 [M+H]$^+$, that was used in the subsequent step, without further purification.

Method D (3R,5S)-3,5-dimethyl-1-[5-(methyloxy)-6-nitro-2-pyridinyl]piperazine (D6, Method B) (0.5 g, 2.25 mmol) was dissolved in methanol (50 mL) and hydrogenated over 10% palladium on carbon (0.25 g, paste) at atmospheric pressure. After 2 hours, the reaction mixture was filtered and evaporated to give the title compound as a pale yellow oil (D7) (yield assumed quantitative), MS (ES$^+$) m/e 237 [M+H]$^+$.

Method E (3R,5S)-3,5-dimethyl-1-[5-(methyloxy)-6-nitro-2-pyridinyl]piperazine (D6, Method D) (4.30 g, 16.6 mmol) was dissolved in methanol (150 mL) and hydrogenated over 10% palladium on carbon (1 g, paste) at atmospheric pressure. After 3 hours, the reaction mixture was filtered and evaporated to give the title compound as a very dark brown oil (D7) (4.31 g), MS (ES$^+$) m/e 237 [M+H]$^+$.

Description 8: 4-Bromo-N-[6-[cis-3,5-dimethyl-1-piperazinyl]-3-(methyloxy)-2-pyridinyl]-3-fluorobenzenesulfonamide (D8)

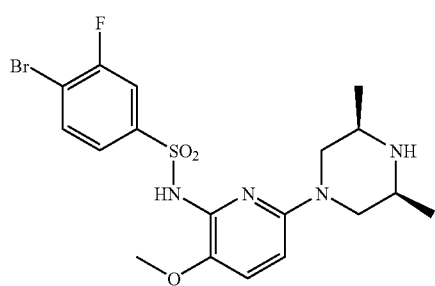

Method A

The title compound was prepared in a similar manner to (D1) replacing 2-amino-6-bromopyridine with (D7, Method A). (D8) MS (ES$^+$) m/e 473, 475 [M+H]$^+$.

Method B

To a stirred solution of 6-[(3R,5S)-3,5-dimethyl-1-piperazinyl]-3-(methyloxy)-2-pyridinamine (D7, Method B) (39.5 g, 167 mmol) in pyridine (300 mL) and dichloromethane (150 mL) was added over 40 mins a solution of 4-bromo-3-fluorobenzenesulfonyl chloride (54.9 g, 201 mmol) in dichloromethane (150 mL) under argon at ambient temperature. After stirring the mixture for 3 h, 18° C. it was concentrated in vacuo to a dark residue. This residue was dissolved in dichloromethane (700 ml) and the solution washed with 0.3M sodium hydroxide (1.6 L). The aqueous phase was further extracted with dichloromethane (2×500 mL). The combined organic extracts were then washed with 0.2M sodium hydroxide (500 mL) and back-extracted with dichloromethane (200 mL). The combined aqueous washes (containing the product), at pH14, was adjusted to pH6 with 5M hydrochloric acid (approx 70 ml) to give a grey precipitate. This solid was filtered and washed with water (3×150 mL) and dried at 30° C. under vacuum over the weekend (54.4 g). The material was stirred with boiling methanol (6 L), filtered from a small amount of undissolved solid, and the filtrate concentrated in vacuo to a volume of 1.5 L. After cooling in ice, this solution afforded a crystalline solid which was filtered off and washed with methanol/diethyl ether (1:1), then diethyl ether and finally dried at 40° C. under vacuum for 1 h (30.7 g, 64.9 mmol, 39%), MS (ES$^+$) m/e 474/476 [M+H]$^+$.

Description 9: 4-Chloro-2-pyrimidinamine

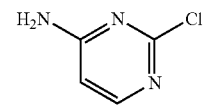

0.880 ammonia (50 ml) was slowly added to a suspension of 2,4-dichloropyrimidine (5.0 g, 33.6 mmol) in ethanol (50 ml) and the resulting mixture was stirred at room temperature for 5 h. It was concentrated under reduced pressure to 25 ml and the resulting solid was filtered, washed with water and dried in a vacuum oven for 4 h. The resulting mixture of the title compound (D9), MS (ES$^+$) m/e 130, 132 and 2-chloro-4-pyrimidinamine MS (ES$^+$) m/e 130, 132 was used without further purification in the next reaction.

Description 10: 4-Bromo-N-(2-[cis-3,5-dimethyl-1-piperazinyl]-4-pyrimidinyl)-3-fluorobenzenesulfonamide

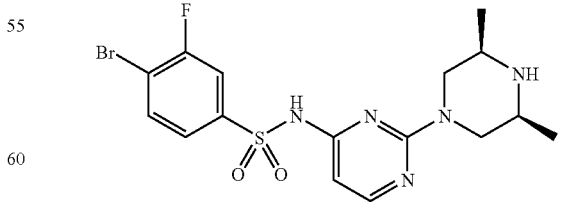

A mixture of the crude product from Description 9 (500 mg, 3.9 mmol) and cis-2,6-dimethylpiperazine (885 mg, 7.8 mmol) in pyridine (2 ml) was microwaved at 100° C. for 10 min. The resulting mixture was azeotroped with toluene and dried to give a mixture of 4-[cis-3,5-dimethyl-1-piperazinyl]-2-pyrimidinamine and 2-[cis-3,5-dimethyl-1-piperazinyl]-4-pyrimidinamine.

The residue (250 mg, 1.2 mmol) was redissolved in pyridine (3 ml) and 4-bromo-3-fluorobenzene sulfonyl chloride (160 ul, 295 mg, 1.44 mmol) was added. The resulting mixture was stirred at room temperature overnight. Additional 4-bromo-3-fluorobenzene sulfonyl chloride (100 ul, 0.75 mmol or eq?) was then added and the mixture was heated to 80° C. for 3 h. The reaction mixture was concentrated under reduced pressure, loaded onto an SCX cartridge and eluted with methanol and 2N $NH_3$ in methanol. The basic fractions were combined, evaporated and purified by column chromatography eluting with 0-20% 2N $NH_3$ in methanol in dichloromethane to afford the title compound (D10), MS (ES$^+$) m/e 444, 446 [M+H]$^+$.

Description 11: 4-Bromo-2-chloro-N-[6-[(3R,5S)-3,5-dimethyl-1-piperazinyl]-3-(methyloxy)-2-pyridinyl]benzenesulfonamide (D11)

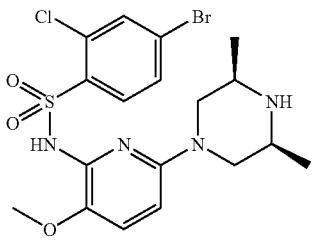

6-[cis-3,5-dimethyl-1-piperazinyl]-3-(methyloxy)-2-pyridinamine (D7, Method C) (473 mg, 2 mmol) was dissolved in pyridine (5 ml) and dichloromethane (5 ml). 4-Bromo-2-chlorobenzene sulfonyl chloride (870 mg, 3 mmol) was added and the solution stirred at room temperature for 5 hours. The mixture was concentrated in vacuo and azeotroped with methanol. The residue was loaded on to an SCX cartridge (Varian, 10 g) in methanol, washed with methanol and the basic products eluted with 2M ammonia/methanol. The product containing fractions were concentrated in vacuo and purified by flash chromatography (Biotage SP4, 40+S, 0-20% 2M ammonia/methanol in dichloromethane to afford the title product (D11), 478 mg, MS (ES$^+$) m/e 489/491/493 [M+H]$^+$.

Description 12: 1,1-Dimethylethyl (2R,6S)-4-[6-amino-5-(methyloxy)-2-pyridinyl]-2,6-dimethyl-1-piperazinecarboxylate (D12)

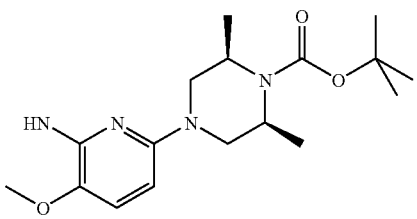

6-[(3R,5S)-3,5-Dimethyl-1-piperazinyl]-3-(methyloxy)-2-pyridinamine (D7, Method C) (1.37 g, 5.8 mmol) was suspended in DCM (60 mL) and cooled to 0° C. Triethylamine (0.892 mL, 6.41 mmol) was added, followed by di-tert-butyl dicarbonate (1.39 g, 6.41 mmol) and the reaction stirred at 0° C. for 2 hours then allowed to warm to room temperature and stirred for 72 hours. The reaction mixture was diluted with DCM to 150 mL and washed with saturated sodium hydrogen carbonate (2×100 mL) and brine (100 mL). The organic layer was dried (MgSO$_4$) and evaporated to give a dark brown oil which was chromatographed [silica gel, eluting with 0 to 60% Ethyl acetate/pentane]. Product fractions evaporated to give the title compound as a yellow oil (D12) (1.0 g), MS (ES$^+$) m/e 337 [M+H]$^+$.

Description 13: 1,1-Dimethylethyl (2R,6S)-4-[6-{[(4-bromo-2-chlorophenyl)sulfonyl]amino}-5-(methyloxy)-2-pyridinyl]-2,6-dimethyl-1-piperazinecarboxylate (D13)

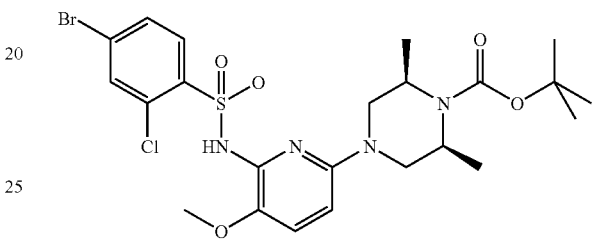

1,1-Dimethylethyl (2R,6S)-4-[6-amino-5-(methyloxy)-2-pyridinyl]-2,6-dimethyl-1-piperazinecarboxylate (D12)(1.0 g, 2.97 mmol) was dissolved in DCM (10 mL) and pyridine (10 mL) and then cooled to 0° C. 4-Bromo-2-chlorobenzenesulfonyl chloride (0.946 g, 3.27 mmol), dissolved in DCM (5 mL) was then added dropwise and the reaction then allowed to warm to rt overnight. The reaction was then evaporated to a minimum and redissolved in DCM (100 mL) and washed with water (50 mL). Aqueous layer was extracted with DCM (2×50 mL) and combined organic extracts washed with brine (100 mL). The organic layer was dried (MgSO$_4$) and evaporated to give a dark oil which was purified by chromatography [silica gel, eluting with 0 to 50% Ethyl acetate/pentane]. Product fractions evaporated to give a yellow crunchy foam (D13) (1.29 g), MS (ES$^+$) m/e 589/591 [M+H]$^+$.

Description 14: 1,1-Dimethylethyl (2R,6S)-4-[6-({[2-chloro-4-(4-methyl-2-thienyl)phenyl]sulfonyl}amino)-5-(methyloxy)-2-pyridinyl]-2,6-dimethyl-1-piperazinecarboxylate (D14)

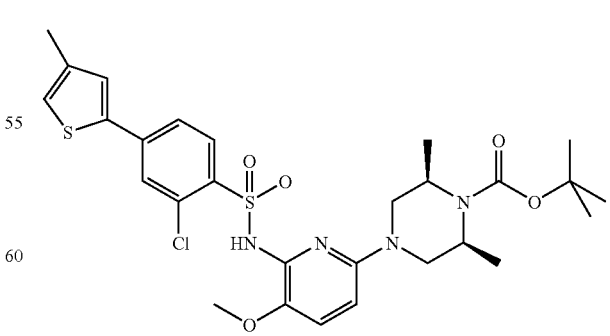

1,1-Dimethylethyl (2R,6S)-4-[6-{[(4-bromo-2-chlorophenyl)sulfonyl]amino}-5-(methyloxy)-2-pyridinyl]-2,6-dimethyl-1-piperazinecarboxylate (D13) (0.15 g, 0.254 mmol), 4-methylthiophene-2-boronic acid (0.054 g, 0.382 mmol), (1,1'-Bis(diphenylphosphino)ferrocene)palladium (II) chloride, DCM complex (9.2 mg, 0.0127 mmol), sodium carbonate (0.053 g, 0.508 mmol) were heated in DME (2 mL) and water (1 mL) at 120° C. in the microwave for 20 minutes. The reaction was then diluted with ethyl acetate (50 mL) and washed with saturated sodium hydrogen carbonate (2×30 mL) and brine (30 mL). The organic layer was dried (MgSO$_4$) and evaporated to give a dark brown oil which was purified by chromatography [silica gel, eluting with 0 to 50% Ethyl acetate/pentane]. Product fractions evaporated to give a pale yellow foam (D14) (0.127 g) MS (ES$^+$) m/e 607/609 [M+H]$^+$.

Description 15: 1,1-Dimethylethyl (2R,6S)-4-[6-({[2-chloro-4-(3-furanyl)phenyl]sulfonyl}amino)-5-(methyloxy)-2-pyridinyl]-2,6-dimethyl-1-piperazinecarboxylate (D15)

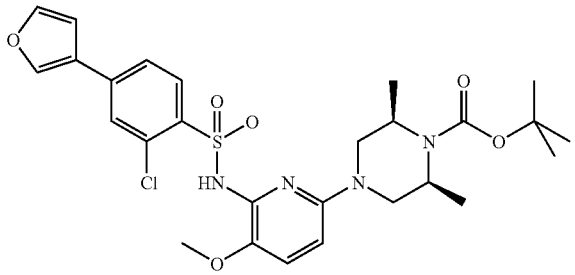

1,1-Dimethylethyl (2R,6S)-4-[6-{[(4-bromo-2-chlorophenyl)sulfonyl]amino}-5-(methyloxy)-2-pyridinyl]-2,6-dimethyl-1-piperazinecarboxylate (D13) (0.15 g, 0.254 mmol), 2-(3-furanyl)-4,4,5,5-tetramethyl-1,3,2-dioxaborolane (0.0739 g, 0.381 mmol), Palladium dichloride di-triphenylphosphine (9.0 mg, 0.0127 mmol), sodium carbonate (0.053 g, 0.508 mmol) were heated in DME (2 mL) and water (1 mL) at 120° C. in the microwave for 20 minutes. The reaction was then diluted with ethyl acetate (50 mL) and washed with saturated sodium hydrogen carbonate (2×30 mL) and brine (30 mL). The organic layer was dried (MgSO$_4$) and evaporated to give a yellow oil which was purified by chromatography [silica gel, eluting with 0 to 60% Ethyl acetate/pentane]. Product fractions evaporated to give a pale yellow foam (D15) (0.170 g) MS (ES$^+$) m/e 577/579 [M+H]$^+$.

Description 16: 1,1-Dimethylethyl (2R,6S)-4-[6-({[2-chloro-4-(5-methyl-2-thienyl)phenyl]sulfonyl}amino)-5-(methyloxy)-2-pyridinyl]-2,6-dimethyl-1-piperazinecarboxylate (D16)

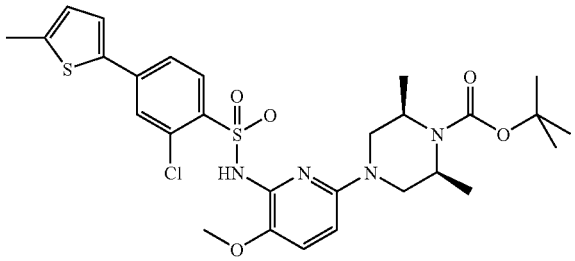

1,1-Dimethylethyl (2R,6S)-4-[6-{[(4-bromo-2-chlorophenyl)sulfonyl]amino}-5-(methyloxy)-2-pyridinyl]-2,6-dimethyl-1-piperazinecarboxylate (D13) (0.10 g, 0.169 mmol), 5-methylthiophen-2-boronic acid (0.0739 g, 0.254 mmol), Palladium dichloride di-triphenylphosphine (5.9 mg, 0.0127 mmol), sodium carbonate (0.0359 g, 0.339 mmol) were heated in DME (1 mL) and water (0.5 mL) at 120° C. in the microwave for 20 minutes. The reaction was then diluted with ethyl acetate (50 mL) and washed with saturated sodium hydrogen carbonate (2×30 mL) and brine (30 mL). The organic layer was dried (MgSO$_4$) and evaporated to give a yellow foam which was purified by chromatography [silica gel, eluting with 0 to 70% Ethyl acetate/pentane]. Product fractions evaporated to give a pale yellow oil (D16) (0.088 g) MS (ES$^+$) m/e 607/609 [M+H]$^+$.

Description 17: 4-Bromo-N-[6-[(3R,5S)-3,5-dimethyl-1-piperazinyl]-3-(methyloxy)-2-pyridinyl]benzenesulfonamide (D17)

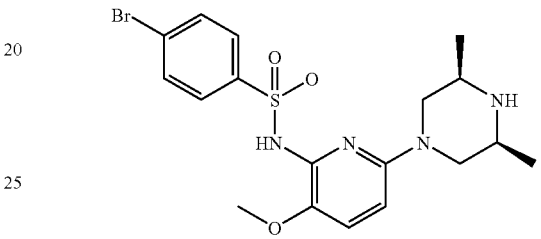

6-[(3R,5S)-3,5-Dimethyl-1-piperazinyl]-3-(methyloxy)-2-pyridinamine (D7, Method E)(1.5 g, 6.35 mmol) was dissolved in DCM (15 mL) and pyridine (15 mL) and then cooled to 0° C. 4-Bromobenzenesulfonyl chloride (3.04 g, 11.9 mmol), dissolved in DCM (8 mL) was then added dropwise and the reaction then allowed to warm to room temperature overnight. The reaction was then evaporated to a minimum and redissolved in DCM (100 mL) and washed with water (50 mL). Aqueous layer was extracted with DCM (100 mL) and combined organic extracts washed with saturated sodium hydrogen carbonate (2×100 mL) and brine (100 mL). The organic layer was dried (MgSO$_4$) and evaporated to give a brown solid which was triturated with ethyl acetate (3×10 mL) to give the title compound as a pale yellow powder (D17) (1.382 g). MS (ES$^+$) m/e 455/457 [M+H]$^+$.

Description 18: (3R,5S)-1-[6-[(4-Bromo-2-fluorophenyl)sulfonyl]-5-(methyloxy)-2-pyridinyl]-3,5-dimethylpiperazine (D18)

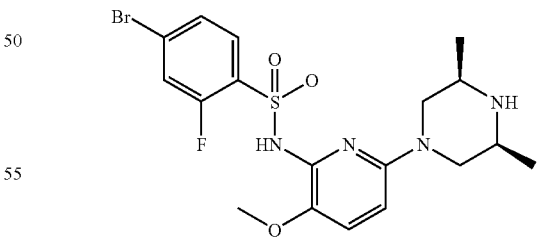

6-[(3R,5S)-3,5-Dimethyl-1-piperazinyl]-3-(methyloxy)-2-pyridinamine (D7, Method D) (2.25 mmol) was dissolved in DCM (5 mL) and pyridine (5 mL) and then cooled to 0° C. 4-Bromo-2-fluoro benzenesulfonyl chloride (0.738 g, 2.706 mmol), dissolved in DCM (5 mL) was then added dropwise and the reaction then allowed to warm to rt overnight. The reaction was then evaporated to a minimum and redissolved in DCM (100 mL) and washed with water (2×75 mL), saturated sodium hydrogen carbonate (3×75 mL) and brine (75 mL). The organic layer was dried (MgSO₄) and evaporated to give a brown oil which was triturated with methanol and dried at 50° C. under high vac to give the title compound as a pale brown powder (D18) (0.400 g). MS (ES⁺) m/e 473/475 [M+H]⁺.

Description 19: cis-1-(2-Chloro-4-pyridinyl)-3,5-dimethylpiperazine

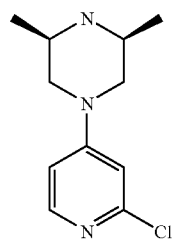

A mixture of 4-bromo-2-chloropyridine (2.0 g, 10.4 mmol), cis-2,6-dimethylpiperazine (1.3 g, 11.4 mmol), sodium t-butoxide (2.0 g, 20.8 mmol), tris(dibenzylideneacetone)dipalladium(0) (230 mg, 2.55 mol %), and 2-dicyclohexylphosphino-2'-(N,N-dimethylamino)biphenyl (230 mg, 5 mol %) in dioxan (20 ml) was stirred at 100° C. for 1 hour. The mixture was cooled to room temperature, filtered through 'celite' and the solvent evaporated. Purification by flash chromatography eluting with 0-5% methanol in dichloromethane gave the title compound (D19). ¹H NMR CDCl₃ ppm δ 1.15 (6H d), 2.42-2.45 (2H, m), 2.90-2.97 (2H, d), 3.61-3.67(2H, m), 6.56 (1H, d), 6.64 (1H, s), 8.00 (1H, s).

Description 20: 4-[cis-3,5-Dimethyl-1-piperazinyl]-N-(diphenylmethylidene)-2-pyridinamine

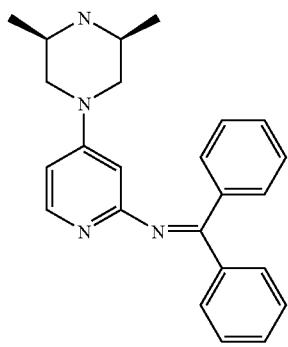

The title compound was prepared in a similar manner to cis-1-(2-chloro-4-pyridinyl)-3,5-dimethylpiperazine (D19) using cis-1-(2-chloro-4-pyridinyl)-3,5-dimethylpiperazine (D19) and benzophenone imine as the starting materials. MS (ES⁺) m/e 371 [M+H]⁺.

Description 21: 4-[cis-3,5-Dimethyl-1-piperazinyl]-2-pyridinamine

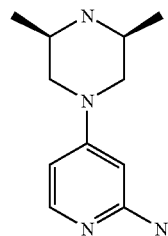

A solution of 4-[cis-3,5-dimethyl-1-piperazinyl]-N-(diphenylmethylidene)-2-pyridinamine (D₂₀) (650 mg, 1.76 mmol) in tetrahydrofuran (5 ml) was treated with 1.0M hydrochloric acid (5 ml) and the mixture stirred at room temperature for 1 hour. The mixture was diluted with water and washed with diethyl ether. The aqueous phase was basified with 50% aq. sodium hydroxide then saturated with sodium chloride. The mixture was extracted with ethyl acetate (×2). The combined extracts were dried and evaporated to give the title compound (D21). ¹H NMR CDCl₃ ppm δ (6H, d), 2.33-0.238 (2H, m), 2.91-2.96 (2H, m), 3.58-3.62 (2H, m), 5.85 (1H, s), 6.18-6.20 (1H, m), 7.78-8.00 (1H, d).

Description 22: 4-Bromo-N-{4-[cis-3,5-dimethyl-1-piperazinyl]-2-pyridinyl}-3-fluorobenzenesulfonamide

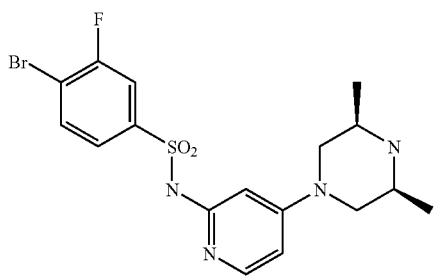

The title compound was prepared in a manner similar to 4-bromo-N-(2-chloro-4-pyridinyl)benzenesulfonamide (D3) using 4-[cis-3,5-dimethyl-1-piperazinyl]-2-pyridinamine (D21) and 4-bromo-3-fluorobenzenesulfonyl chloride as the starting materials. MS (ES⁺) m/e 443, 445 [M+H]⁺.

Description 23: 1,1-Dimethylethyl 5-bromo-2-(methyloxy)-3-pyridinecarboxylate

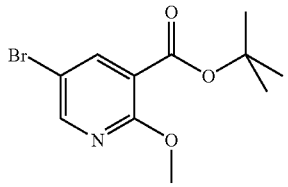

A suspension of 5-bromo-2-methoxy-3-pyridine carboxylic acid (9.3 g, 40 mmol) in toluene (100 ml) was treated with N,N-dimethylformamide di-t-butylacetal (16.3 g, 80 mmol) and the mixture heated at 80° C. for 2 hours. The mixture was cooled and the solvents evaporated. The residue was dissolved in ethyl acetate and washed with water (×2). The organic phase was dried and evaporated to give the title compound (D23). $^1$H NMR CDCl$_3$ ppm δ 1.58 (9 h, s), 4.01 (3H, s), 8.14 (1H, s), 8.3 (1H, s).

Description 24: 1,1-Dimethylethyl 5-[cis-3,5-dimethyl-1-piperazinyl]-2-(methyloxy)-3-pyridinecarboxylate

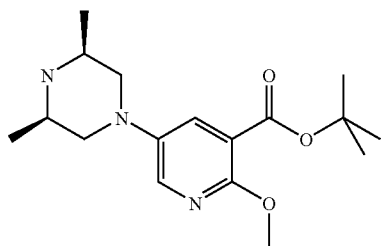

The title compound was prepared in a similar manner to cis-1-(2-chloro-4-pyridinyl)-3,5-dimethylpiperazine (D19) using 1,1-dimethylethyl 5-bromo-2-(methyloxy)-3-pyridinecarboxylate (D23) and cis-2,2-dimethylpiperazine as the starting materials.

Description 25: 1,1-Dimethylethyl 5-[cis-3,5-dimethyl-4-(phenylmethyl)-1-piperazinyl]-2-(methyloxy)-3-pyridinecarboxylate

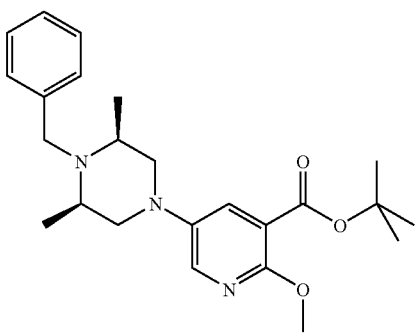

A mixture of 1,1-dimethylethyl 5-[cis-3,5-dimethyl-1-piperazinyl]-2-(methyloxy)-3-pyridinecarboxylate (D24) (500 mg, 1.56 mmol), potassium carbonate (430 mg, 3.12 mmol) and benzyl bromide (266 mg, 1.56 mmol) in N,N-dimethylformamide (10 ml) was stirred at 80° C. for 4 hours. The reaction mixture was partitioned between ethyl acetate and water. The organic phase washed with water, dried and evaporated. Purification by flash chromatography eluting with 5-20% ethyl acetate in hexanes gave the title compound (D25). MS (ES$^+$) m/e 412 [M+H]$^+$.

Description 26: 5-[cis-3,5-Dimethyl-4-(phenylmethyl)-1-piperazinyl]-2-(methyloxy)-3-pyridinecarboxylic acid

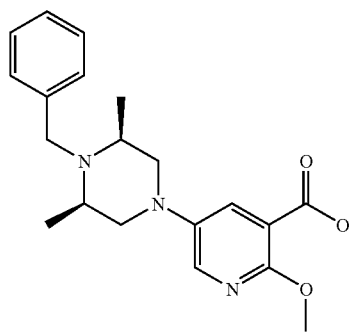

A solution of 1,1-dimethylethyl 5-[cis-3,5-dimethyl-4-(phenylmethyl)-1-piperazinyl]-2-(methyloxy)-3-pyridinecarboxylate (D25) in dichloromethane (5 ml) was treated with trifluoroacetic acid (5 ml) and the mixture stirred at room temperature for 2 hours. The solvents were evaporated and the residue purified on SCX eluting with 2M ammonia in methanol to give the title compound (D26). MS (ES$^+$) m/e 356 [M+H]$^+$.

Description 27: 1,1-Dimethylethyl [5-[(3-cis-3,5-dimethyl-4-(phenylmethyl)-1-piperazinyl]-2-(methyloxy)-3-pyridinyl]carbamate

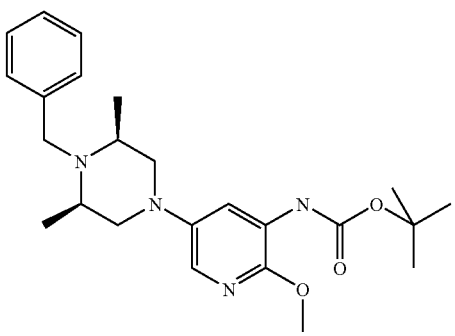

A mixture of 5-[cis-3,5-dimethyl-4-(phenylmethyl)-1-piperazinyl]-2-(methyloxy)-3-pyridinecarboxylic acid (D26) (100 mg, 0.28 mmol), diphenylphosphoryl azide (115 mg, 0.42 mmol), and triethylamine (85 mg, 0.84 mmol) in t-butanol (3 ml) and toluene (3 ml) was heated at 65° C. for 1 hour then at 110° C. for 24 hours. The reaction mixture was cooled to room temperature and the solvents evaporated. Purification by flash chromatography eluting with 5-25% ethyl acetate in hexanes gave the title compound (D27). MS (ES$^+$) m/e 427 [M+H]$^+$.

Description 28: N-[5-[cis-3,5-Dimethyl-4-(phenylmethyl)-1-piperazinyl]-2-(methyloxy)-3-pyridinyl]-2,2,2-trifluoroacetamide

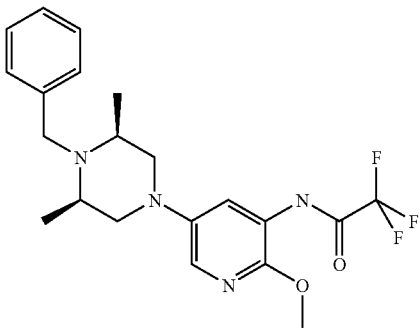

A solution of 1,1-dimethylethyl [5-[cis-3,5-dimethyl-4-(phenylmethyl)-1-piperazinyl]-2-(methyloxy)-3-pyridinyl]carbamate (D27) (119 mg, 0.28 mmol) in dichloromethane (2 ml) was treated with trifluoroacetic acid (2 ml) and stirred at room temperature for 2 hours. The solvent was evaporated and the residue azeotroped with toluene (×2) to give the title compound (D28). MS (ES$^+$) m/e 423 [M+H]$^+$.

Description 29: 5-[cis-3,5-Dimethyl-4-(phenylmethyl)-1-piperazinyl]-2-(methyloxy)-3-pyridinamine

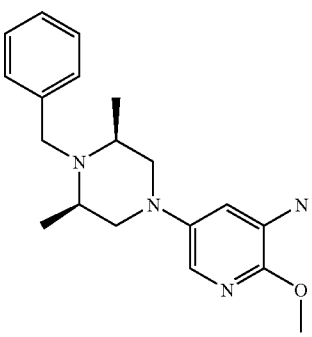

A solution of N-[5-[cis-3,5-dimethyl-4-(phenylmethyl)-1-piperazinyl]-2-(methyloxy)-3-pyridinyl]-2,2,2-trifluoroacetamide (D28) (97 mg, 0.28 mmol) in methanol (5 ml) was treated with potassium carbonate (500 mg, large excess). The mixture was stirred at room temperature for 24 hours. The mixture was diluted with ethyl acetate and washed with water and brine. The organic phase was dried and evaporated to give the title compound (D29) which was used without further purification.

Description 30: 4-Bromo-N-[(4-bromo-3-fluorophenyl)sulfonyl]-N-[5-[cis-3,5-dimethyl-4-(phenylmethyl)-1-piperazinyl]-2-(methyloxy)-3-pyridinyl]-3-fluorobenzenesulfonamide

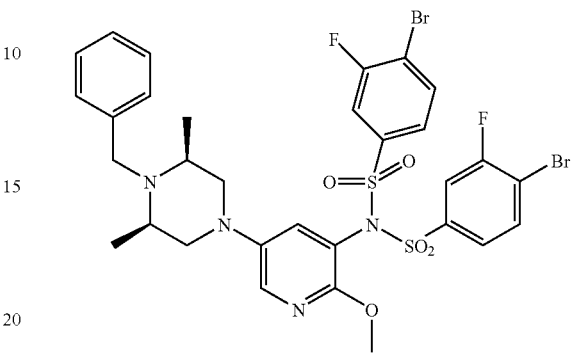

The title compound was prepared in a manner similar to 4-bromo-N-(2-chloro-4-pyridinyl)benzenesulfonamide (D3) using 5-[cis-3,5-dimethyl-4-(phenylmethyl)-1-piperazinyl]-2-(methyloxy)-3-pyridinamine (D29) and 4-bromo-3-fluorobenzenesulfonyl chloride as the starting materials. MS (ES$^+$) m/e 799, 801, 803 [M+H]$^+$.

Description 31: N-[5-[cis-3,5-Dimethyl-4-(phenylmethyl)-1-piperazinyl]-2-(methyloxy)-3-pyridinyl]-3-fluoro-4-(5-methyl-2-furanyl)benzenesulfonamide

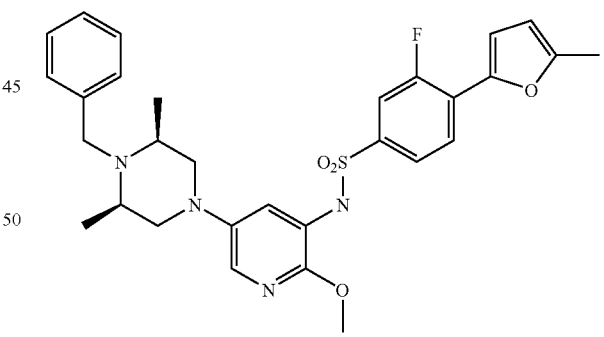

The title compound was prepare in a manner similar to Example 1(E1) using 4-bromo-N-[(4-bromo-3-fluorophenyl)sulfonyl]-N-[5-[cis-3,5-dimethyl-4-(phenylmethyl)-1-piperazinyl]-2-(methyloxy)-3-pyridinyl]-3-fluorobenzenesulfonamide (D30) as the starting material. MS (ES$^+$) m/e 565 [M+H]$^+$.

Description 32: Ethyl 5-[cis-3,5-dimethyl-1-piperazinyl]-3-pyridinecarboxylate

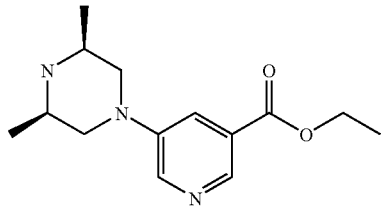

The title compound was prepared in a similar manner to cis-1-(2-chloro-4-pyridinyl)-3,5-dimethylpiperazine using ethyl 5-bromo-3-pyridinecarboxylate and cis-2,2-dimethylpiperazine as the starting materials (D19). MS (ES⁺) m/e 264 [M+H]⁺.

Description 33: 5-[cis-3,5-Dimethyl-1-piperazinyl]-3-pyridinecarboxylic acid

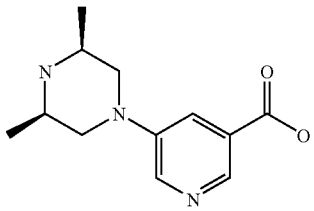

A solution of ethyl 5-[(3R,5S)-3,5-dimethyl-1-piperazinyl]-3-pyridinecarboxylate (D32) (800 mg, 3 mmol) in tetrahydrofuran (5 ml) was treated with 0.5M lithium hydroxide (12 ml, 6 mmol). The mixture was stirred at room temperature for 2 hours. The reaction was quenched with acetic acid (1 ml). The solvent was evaporated and the residue purified on SCX eluting with 2M ammonia in methanol to give the title compound (D33). MS (ES⁺) m/e 236 [M+H]⁺.

Description 34: 1,1-Dimethylethyl {5-[cis-3,5-dimethyl-1-piperazinyl]-3-pyridinyl}carbamate

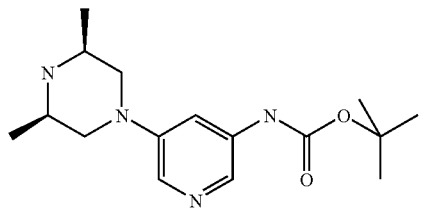

The title compound was prepared in a manner similar to 1,1-dimethylethyl [5-[(3-cis-3,5-dimethyl-4-(phenylmethyl)-1-piperazinyl]-2-(methyloxy)-3-pyridinyl]carbamate (D26) using 5-[cis-3,5-dimethyl-1-piperazinyl]-3-pyridinecarboxylic acid (D33) as the starting material. MS (ES⁺) m/e 307 [M+H]⁺.

Description 35: N-{5-[cis-3,5-Dimethyl-1-piperazinyl]-3-pyridinyl}-2,2,2-trifluoroacetamide

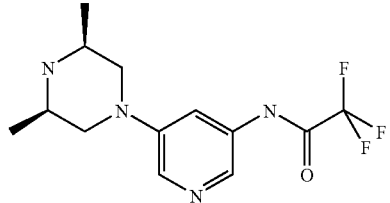

The title compound was prepared in a manner similar to N-[5-[cis-3,5-dimethyl-4-(phenylmethyl)-1-piperazinyl]-2-(methyloxy)-3-pyridinyl]-2,2,2-trifluoroacetamide (D28) using 1,1-dimethylethyl {5-[cis-3,5-dimethyl-1-piperazinyl]-3-pyridinyl}carbamate (D34) as the starting material. MS (ES⁺) m/e 303 [M+H]⁺.

Description 36: 5-[(3R,5S)-3,5-Dimethyl-1-piperazinyl]-3-pyridinamine

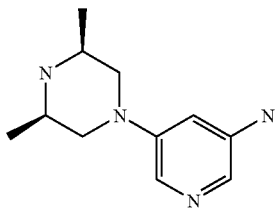

The title compound was prepared in a manner similar to 5-[cis-3,5-dimethyl-4-(phenylmethyl)-1-piperazinyl]-2-(methyloxy)-3-pyridinamine (D29) using N-{5-[cis-3,5-dimethyl-1-piperazinyl]-3-pyridinyl}-2,2,2-trifluoroacetamide (D35) as the starting material.

Description 37: 4-Bromo-N-{5-[cis-3,5-dimethyl-1-piperazinyl]-3-pyridinyl}-3-fluorobenzenesulfonamide

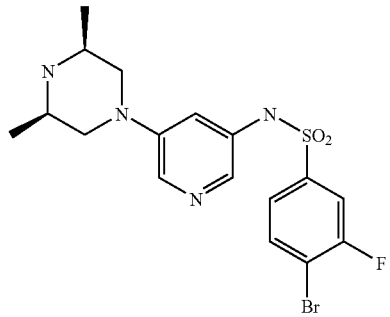

The title compound was prepared in a manner similar to 4-bromo-N-(2-chloro-4-pyridinyl)benzenesulfonamide (D3) using 5-[cis-3,5-dimethyl-1-piperazinyl]-3-pyridinamine (D36) and 4-bromo-3-fluorobenzenesulfonyl chloride as the starting materials.

Description 38: Ethyl 5-[(3R,5S)-3,5-dimethyl-4-(phenylmethyl)-1-piperazinyl]-2-(methyloxy)-3-pyridinecarboxylate

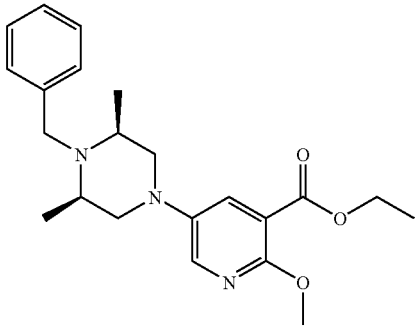

The title compound was prepared in a similar manner to cis-1-(2-chloro-4-pyridinyl)-3,5-dimethylpiperazine (D19) using ethyl 5-bromo-2-(methyloxy)-3-pyridinecarboxylate and 1-benzyl-(cis-2,2-dimethyl)piperazine as the starting materials. MS (ES+) m/e 384 [M+H]+.

Description 39: 5-[(3R,5S)-3,5-Dimethyl-4-(phenylmethyl)-1-piperazinyl]-2-(methyloxy)-3-pyridinecarboxylic acid

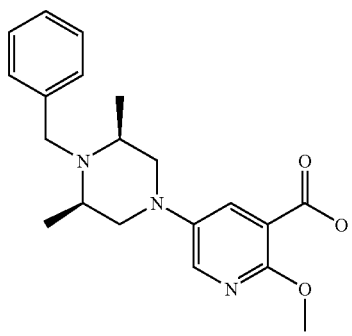

A solution of ethyl 5-[(3R,5S)-3,5-dimethyl-4-(phenylmethyl)-1-piperazinyl]-2-(methyloxy)-3-pyridinecarboxylate (D38)(3.4 g, 8.9 mmol) in ethanol (10 ml) and 2M sodium hydroxide (10 ml) was heated at 60° C. for 2 hours. The ethanol was evaporated and the residue diluted with water, the mixture was acidified with glacial acetic acid and extracted with ethyl acetate (×2). The combined extracts were dried and evaporated. Purification on SCX eluting with 2M ammonia in methanol gave the title compound (D39). MS (ES+) m/e 356 [M+H]+.

Example 1

N-(6-[cis-3,5-Dimethyl-1-piperazinyl]-2-pyridinyl)-3-fluoro-4-(5-methyl-2-furanyl)benzenesulfonamide hydrochloride (E1)

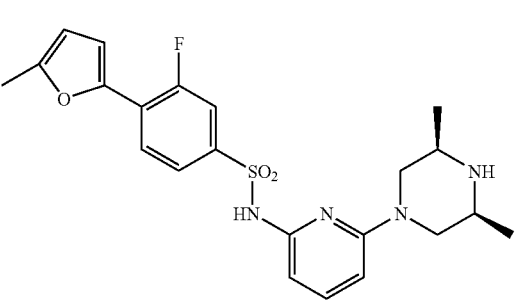

A mixture of 4-bromo-N-(6-[cis-3,5-dimethyl-1-piperazinyl]-2-pyridinyl)-3-fluorobenzenesulfonamide (D2) (40 mg, 0.09 mmol), 5-methylfuran-2-boronic acid (15 mg, 0.12 mmol), sodium carbonate (35 mg, 0.33 mmol) and dichlorobis(triphenylphosphine) palladium(0) (5 mg, 5 mol %) in 1,2-dimethoxyethane (3 ml) and water (1 ml) was microwaved at 120° C. for 20 min. The reaction mixture was partitioned between diethyl ether (5 ml) and water (2 ml). The organic phase was dried and evaporated. The residue was triturated with diethyl ether and ethyl acetate then dissolved in methanol and converted to the hydrochloride salt by treatment with hydrogen chloride in diethyl ether. Trituration with diethyl ether afforded the title compound (E1), MS (ES+) m/e 445 [M+H]+.

Example 2

N-(2-[cis-3,5-Dimethyl-1-piperazinyl]-4-pyridinyl)-4-(5-methyl-2-furanyl)benzenesulfonamide hydrochloride (E2)

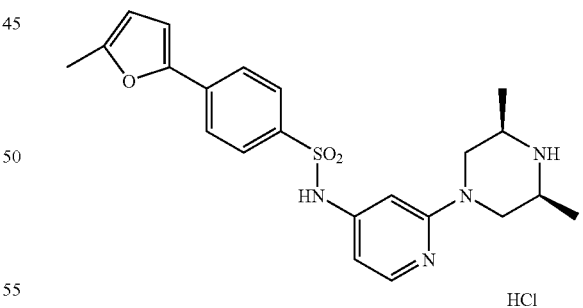

A mixture of N-(2-chloro-4-pyridinyl)-4-(5-methyl-2-furanyl)benzenesulfonamide (D4) (250 mg, 0.74 mmol), cis-2,6-dimethylpiperazine (170 mg, 1.48 mmol), sodium tert-butoxide (140 mg, 1.48 mmol), tris(dibenzylideneacetone)dipalladium(0) (15 mg, 5 mol %), and 2-dicyclohexylphosphino-2'-(N,N-dimethylamino)biphenyl (30 mg, 10 mol %) in dioxan (4 ml) was microwaved at 120° C. for 1 h. The reaction mixture was partitioned between ethyl acetate and water. The aqueous phase was evaporated and the residue purified by column chromatography eluting with 5-10% methanol in dichloromethane. The product was dissolved in methanol and converted to the hydrochloride salt by treatment with hydrogen chloride in diethyl ether to afford the title compound (E2), MS (ES+) m/e 427 [M+H]+.

Example 3

N-[6-[cis-3,5-Dimethyl-1-piperazinyl]-3-(methyloxy)-2-pyridinyl]-3-fluoro-4-(5-methyl-2-furanyl)benzenesulfonamide hydrochloride (E3)

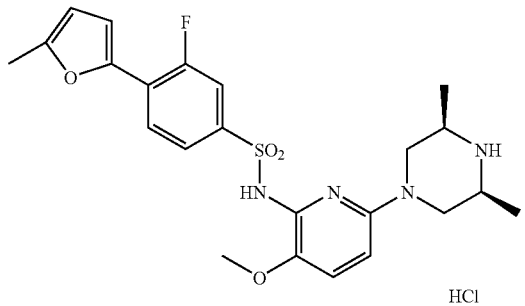

Method A

The title compound was prepared in a similar manner to (E1) replacing (D2) with (D8, Method A). (E3) MS (ES+) m/e 475 [M+H]+.

Method B

To a stirred solution of 4-bromo-N-[6-[(3R,5S)-3,5-dimethyl-1-piperazinyl]-3-(methyloxy)-2-pyridinyl]-3-fluorobenzenesulfonamide (D8, Method B) (29.1 g, 61.5 mmol) in 1,2-dimethoxyethane (290 ml) at ambient temperature under argon was added a solution of sodium carbonate (34.3 g, 324 mmol) in water (145 ml). Palladium dichloride ditriphenylphosphine (0.844 g, 1.2 mmol) was then added to the mixture. This mixture was vigorously stirred and heated to 35° C. at which temperature a solution of 4,4,5,5-tetramethyl-2-(5-methyl-2-furanyl)-1,3,2-dioxaborolane (12.8 g, 61.4 mmol) in 1,2-dimethoxyethane (25 ml) was added over 30 seconds. Heating was continued so that reflux was reached over a period of 1 h. Reflux was then maintained for a further 1 h. After this time a further portion of 4,4,5,5-tetramethyl-2-(5-methyl-2-furanyl)-1,3,2-dioxaborolane (12.8 g, 61.4 mmol) in 1,2-dimethoxyethane (25 ml) was added and reflux was maintained for 0.75 h. The reaction mixture was then cooled to ambient temperature and concentrated to leave a residue. To the residue was added water (1 L) and to this stirred mixture was added 5M hydrochloric acid (approx 55 mL) until the supernatant attained pH7. The resulting solid which precipitated was filtered off under suction through a large diameter glass sinter funnel and washed with water (3×100 mL). The solid was then dried at 40° C. under vacuum for 24 h to give a light brown powder (29 g). A second crop of solid (2.0 g) was collected from the mother liquors.

In a similar manner to that described above, another batch of solid (0.5 g) was prepared from 4-bromo-N-[6-[(3R,5S)-3,5-dimethyl-1-piperazinyl]-3-(methyloxy)-2-pyridinyl]-3-fluorobenzenesulfonamide (D8, Method B)(1.0 g, 2.1 mmol).

All the solids were collected together (31.5 g), stirred with boiling methanol (3.2 L) and filtered through Kieselguhr whilst hot to remove a small quantity of purple-black solid. The filtrate was concentrated in vacuo to a volume of approx 1.5 L and left at room temperature for 0.5 h, then further evaporated in vacuo to a final volume of 250 ml. The mixture was cooled in an ice bath for 1 h and the crystallised solid was filtered, washed with methanol/diethyl ether (1:1)(2×75 mL) then diethyl ether (2×75 mL) and dried at 40° C. under vacuum for 18 h (17.4 g).

To a suspension of this material (17 g) in methanol (400 mL) at ambient temperature was added concentrated hydrochloric acid (3.7 ml). The resulting solution was diluted with more methanol (100 mL) and heated to 55° C., at which temperature it was treated with Isolute Si-Thiol powder (commercial supplier: Biotage)(20 g of grade 1.3 mmol/g) in an attempt to scavenge palladium residues. After 1.5 h at this temperature, the mixture was filtered under suction through Kieselghur. The filtrate was concentrated to a volume of approx 200 ml and with stirring was diluted with diethyl ether (200 mL). After 0.5 h the resulting precipitated solid was filtered off and washed with methanol/diethyl ether (1:1)(80 mL) then diethyl ether (2×100 mL) and dried at 40° C. under vacuum for 1 h (17.3 g). This material was stirred with boiling methanol (350 mL) and the solution concentrated to a volume of 100 mL before cooling in an ice bath for 0.5 h. The pale yellow, crystallised solid was filtered off and washed with methanol/diethyl ether (1:1)(2×30 mL) then diethyl ether (2×50 mL) and dried at 40° C. under vacuum for 18 h.

This material was then heated to 60° C. under vacuum for 21 h to remove all the methanol solvent (12.01 g), (E3).

δH (d6-DMSO, 400 MHz) 1.20 (6H, d, J=6.4 Hz), 2.39 (3H, s), 2.40-2.45 (2H, m), 3.12-3.15 (2H, br, m), 3.76 (3H, s), 3.82-3.86 (2H, m), 6.35-6.36 (1H, m), 6.55 (1H, d, J=9.2 Hz), 6.92-6.93 (1H, m), 7.35 (1H, d, J=8.8 Hz), 7.78-7.80 (2H, m), 7.94 (1H, t, J=8 Hz), 8.8 (1H, br, s), 9.4 (1H, br, s), 10.5 (1H, br, s).

Example 4

N-(2-[cis-3,5-Dimethyl-1-piperazinyl]-4-pyrimidinyl)-3-fluoro-4-(5-methyl-2-furanyl)benzenesulfonamide (E4)

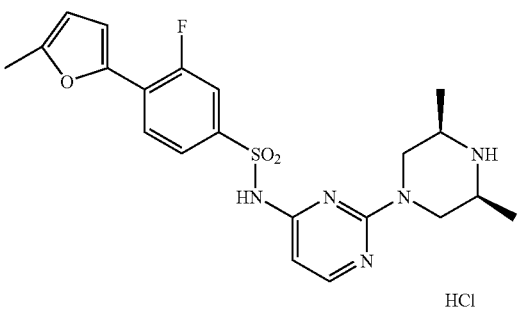

A mixture 4-bromo-N-{2-[cis-3,5-dimethyl-1-piperazinyl]-4-pyrimidinyl}-3-fluorobenzenesulfonamide (D10) (90 mg, 0.2 mmol), 5-methylfuran-2-boronic ester (85 mg, 0.4 mmol), sodium carbonate (86 mg, 0.8 mmol) and dichlorobis(triphenylphosphine) palladium(0) (7 mg, 5 mol %) in 1,2-dimethoxyethane (3 ml) and water (1 ml) was microwaved at 110° C. for 20 min. The reaction mixture was loaded onto a hydromatrix cartridge and eluted with methanol. The methanol was removed under reduce pressure and the residue was loaded onto an SCX cartridge and eluted with methanol and 2N NH₃ in methanol. The basic fractions were combined, evaporated, azeotroped with toluene and the residue was purified by column chromatography eluting with DMAW60 (60:

18:2:3 parts dichloromethane:methanol:acetic acid:water). The product was dissolved in methanol and converted to the hydrochloride salt by treatment with hydrogen chloride in diethyl ether to afford the title compound (E4), MS (ES+) m/e 446 [M+H]+.

Example 5

2-Chloro-N-[6-[(3R,5S)-3,5-dimethyl-1-piperazinyl]-3-(methyloxy)-2-pyridinyl]-4-(5-methyl-2-furanyl)benzenesulfonamide Hydrochloride (E5)

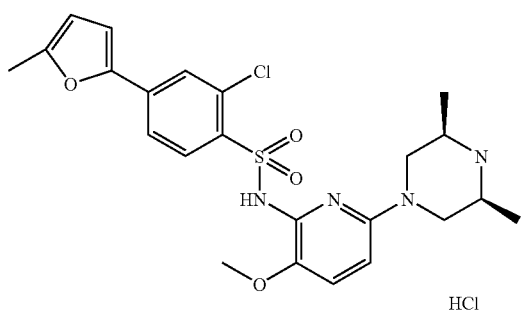

4-Bromo-2-chloro-N-[6-[(3R,5S)-3,5-dimethyl-1-piperazinyl]-3-(methyloxy)-2-pyridinyl]benzenesulfonamide (D11) (245 mg, 0.5 mmol), 4,4,5,5-tetramethyl-2-(5-methyl-furan-2-yl)-[1,3,2]-aloxaboralane (113 mg, 0.55 mmol) and sodium carbonate (212 mg, 2 mmol) were heated at 130° C. in a microwave reactor for 20 minutes in 1,2-dimethoxyethane (4 ml) and water (2 ml). The reaction mixture was partitioned between ethyl acetate and water. The organic phase washed with water (×3), brine, dried over anhydrous sodium sulfate and concentrated in vacuo. The residue was twice purified by flash chromatography (Biotage SP4, 25+S, 0-20% 2M ammonia/methanol in dichloromethane to afford the title product. This was converted to hydrochloride salt (1M hydrogen chloride in diethyl ether and MeOH) to afford the hydrochloride salt of the title product (E5): 90 mg, MS (ES+) m/e 491/493 [M+H]+.

Example 6

2-Chloro-N-[6-[(3R,5S)-3,5-dimethyl-1-piperazinyl]-3-(methyloxy)-2-pyridinyl]-4-(4-methyl-2-thienyl)benzenesulfonamide Hydrochloride (E6)

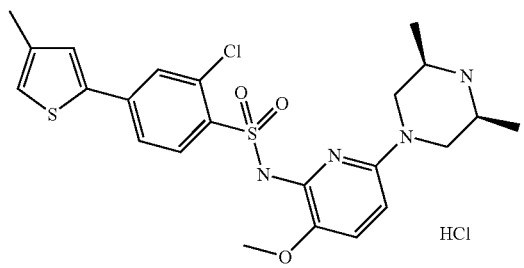

1,1-Dimethylethyl (2R,6S)-4-[6-({[2-chloro-4-(4-methyl-2-thienyl)phenyl]sulfonyl}amino)-5-(methyloxy)-2-pyridinyl]-2,6-dimethyl-1-piperazinecarboxylate (D14) (0.128 g) was dissolved in dioxane (5 mL) and 4N HCl/dioxane (5 mL) added and the reaction stirred at rt for 24 hours. The reaction mixture was evaporated to give the title compound as a pale yellow solid (E6) (0.111 g). MS (ES+) m/e 507/509 [M+H]+.

Example 7

2-Chloro-N-[6-[(3R,5S)-3,5-dimethyl-1-piperazinyl]-3-(methyloxy)-2-pyridinyl]-4-(3-furanyl)benzenesulfonamide Hydrochloride (E7)

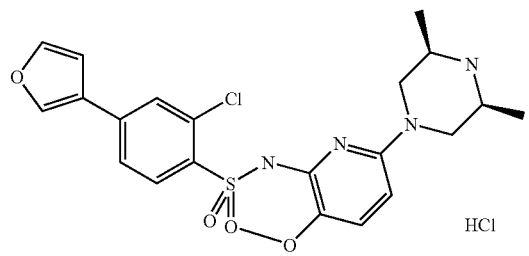

1,1-Dimethylethyl (2R,6S)-4-[6-({[2-chloro-4-(3-furanyl)phenyl]sulfonyl}amino)-5-(methyloxy)-2-pyridinyl]-2,6-dimethyl-1-piperazinecarboxylate (D15) (0.170 g) was dissolved in 4N HCl/dioxane (6 mL) and the reaction stirred at 35° C. for 2 hours. The reaction mixture was evaporated and triturated with ethyl acetate/ether (×3) to give a white solid which was dried at 50° C. under high vac to give the compound as a white solid (E7)(0.119 g). MS (ES+) m/e 477/479 [M+H]+.

Example 8

2-Chloro-N-[6-[(3R,5S)-3,5-dimethyl-1-piperazinyl]-3-(methyloxy)-2-pyridinyl]-4-(5-methyl-2-thienyl)benzenesulfonamide Hydrochloride (E8)

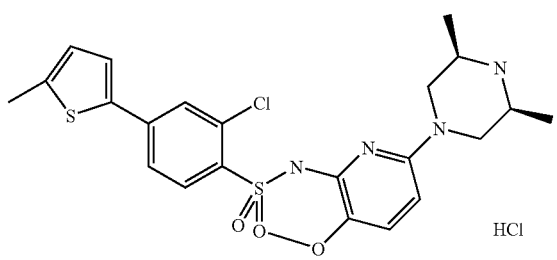

1,1-Dimethylethyl (2R,6S)-4-[6-({[2-chloro-4-(5-methyl-2-thienyl)phenyl]sulfonyl}amino)-5-(methyloxy)-2-pyridinyl]-2,6-dimethyl-1-piperazinecarboxylate (D16) (0.170 g) was dissolved in 4N HCl/dioxane (5 mL) added and the reaction stirred at rt for 24 hours. The reaction mixture was evaporated and triturated with ethyl acetate/ether ×3 to give a white solid which was dried at 50° C. under high vac to give the compound as a white solid (E8)(0.066 g). MS (ES+) m/e 507/509 [M+H]+.

Example 9

N-[6-[(3R,5S)-3,5-dimethyl-1-piperazinyl]-3-(methyloxy)-2-pyridinyl]-4-(5-methyl-2-furanyl)benzenesulfonamide Hydrochloride (E9)

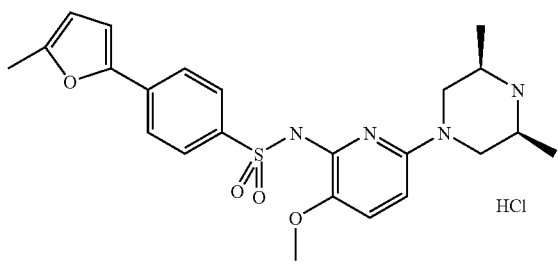

4-Bromo-N-[6-[(3R,5S)-3,5-dimethyl-1-piperazinyl]-3-(methyloxy)-2-pyridinyl]benzenesulfonamide (D17) (0.10 g, 0.219 mmol), 4,4,5,5-tetramethyl-2-(5-methyl-2-furanyl)-1,3,2-dioxaborolane (0.068 g, 0.329 mmol), Palladium dichloride di-triphenylphosphine (7.7 mg, 0.0109 mmol), sodium carbonate (0.084 g, 0.878 mmol) were heated in DME (2 mL) and water (1.0 mL) at 120° C. in the microwave for 20 minutes. The reaction was then diluted with ethyl acetate (20 mL) and washed with saturated sodium hydrogen carbonate (2×15 mL) and brine (15 mL). The organic layer was dried (MgSO$_4$), evaporated and purified by chromatography [silica gel, eluting with 0 to 15% methanol/DCM] over 45 minutes. Product fractions were evaporated, redissolved in DCM and freebase converted to HCl with 1M HCl/ether. The products were evaporated, triturated with ether/acetone and dried at 50° C. under high vac overnight (E9) (0.012 g) MS (ES$^+$) m/e 457 [M+H]$^+$.

Example 10

N-[6-[(3R,5S)-3,5-Dimethyl-1-piperazinyl]-3-(methyloxy)-2-pyridinyl]-2'-fluoro-5'-(methyloxy)-4-biphenylsulfonamide Hydrochloride (E10)

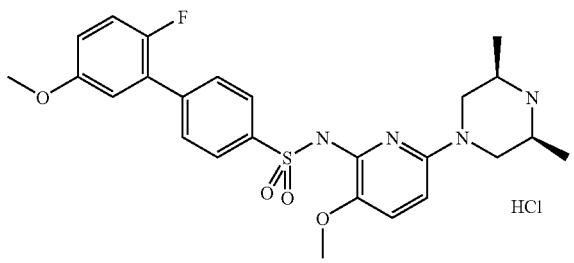

4-Bromo-N-[6-[(3R,5S)-3,5-dimethyl-1-piperazinyl]-3-(methyloxy)-2-pyridinyl]benzenesulfonamide (D17) (0.10 g, 0.219 mmol), 2-fluoro-5-methoxy benzene boronic acid (0.056 g, 0.329 mmol), Palladium dichloride di-triphenylphosphine (7.7 mg, 0.0109 mmol), sodium carbonate (0.084 g, 0.878 mmol) were heated in DME (2 mL) and water (1.0 mL) at 120° C. in the microwave for 20 minutes. The reaction was then diluted with ethyl acetate (20 mL) and washed with saturated sodium hydrogen carbonate (2×15 mL) and brine (15 mL). Organic layer dried (MgSO$_4$), evaporated and purified by chromatography [silica gel, eluting with 0 to 15% methanol/DCM]. Product fractions evaporated, redissolved in DCM and freebase converted to HCl with excess 1M HCl/ether. Evaporated, triturated with ether/acetone and dried at 50° C. under high vac overnight (E10) (0.004 g) MS (ES$^+$) m/e 501 [M+H]$^+$.

Example 11

N-[6-[(3R,5S)-3,5-Dimethyl-1-piperazinyl]-3-(methyloxy)-2-pyridinyl]-2-fluoro-4-(5-methyl-2-furanyl)benzenesulfonamide Hydrochloride (E11)

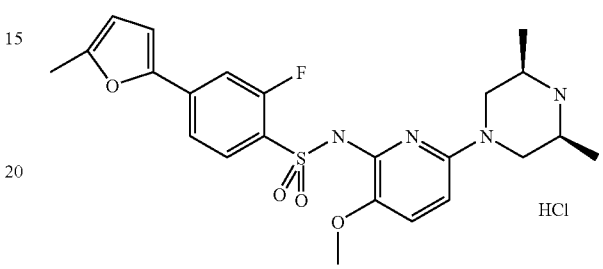

(3R,5S)-1-[6-[[(4-Bromo-2-fluorophenyl)sulfonyl]-5-(methyloxy)-2-pyridinyl]-3,5-dimethylpiperazine (D18) (0.15 g, 0.317 mmol), 4,4,5,5-tetramethyl-2-(5-methyl-2-furanyl)-1,3,2-dioxaborolane (0.098 g, 0.475 mmol), Palladium dichloride di-triphenylphosphine (11.1 mg, 0.0158 mmol), sodium carbonate (0.121 g, 1.268 mmol) were heated in DME (2 mL) and water (1.0 mL) at 120° C. in the microwave for 10 minutes. The reaction mixture was then poured onto SCX-Silica, washed with methanol (80 mL) and eluted with 2M ammonia/methanol solution (80 mL). The eluent was evaporated and purified by chromatography [silica gel, eluting with 0 to 10% methanol/DCM]. Small amount of insoluble material from column combined with evaporated pure product fractions. Product redissolved in DCM and treated with slight excess of 1M HCl/diethyl ether, evaporated and triturated with acetone/diethyl ether to give the title compound as a solid after drying under high vac overnight. (E11) (0.129 g) MS (ES$^+$) m/e 475 [M+H]$^+$.

Example 12

N-{4-[(3R,5S)-3,5-Dimethyl-1-piperazinyl]-2-pyridinyl}-3-fluoro-4-(5-methyl-2-furanyl)benzenesulfonamide Hydrochloride

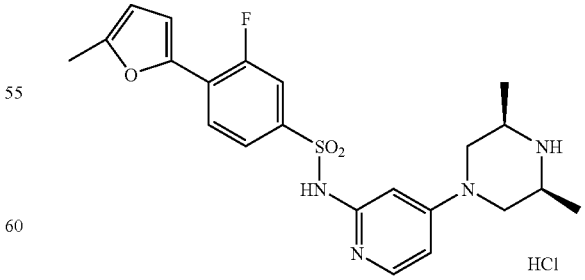

The title compound was prepare in a manner similar to Example 1 (E1) using 4-bromo-N-{4-[cis-3,5-dimethyl-1-piperazinyl]-2-pyridinyl}-3-fluorobenzenesulfonamide (D22) as the starting material. MS (ES$^+$) m/e 445 [M+H]$^+$.

Example 13

N-[5-[cis-3,5-Dimethyl-1-piperazinyl]-2-(methyloxy)-3-pyridinyl]-3-fluoro-4-(5-methyl-2-furanyl)benzenesulfonamide Hydrochloride

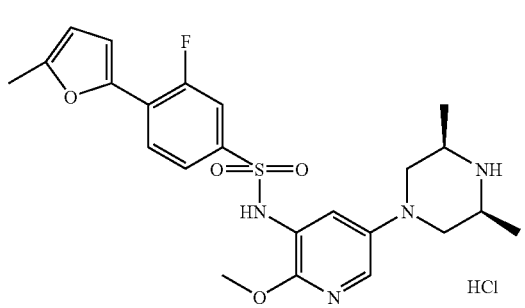

A solution of N-[5-[cis-3,5-dimethyl-4-(phenylmethyl)-1-piperazinyl]-2-(methyloxy)-3-pyridinyl]-3-fluoro-4-(5-methyl-2-furanyl)benzenesulfonamide (D31) (60 mg, 0.1 mmol) in ethanol (5 ml) and 2M hydrochloric acid (0.5 ml) containing 10% palladium on carbon (10 mg) was stirred in a hydrogen atmosphere for 2 hours. The mixture was filtered through 'celite' and the solvent evaporated. Purification of the residue by flash chromatography eluting with 5% methanol in dichloromethane followed by treatment with 1.0M hydrogen chloride in diethyl ether gave the title compound (E13). MS (ES$^+$) m/e 475 [M+H]$^+$.

Example 14

N-{5-[cis-3,5-Dimethyl-1-piperazinyl]-3-pyridinyl}-3-fluoro-4-(5-methyl-2-furanyl)benzenesulfonamide Hydrochloride

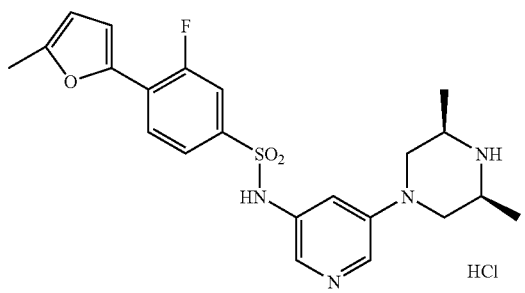

The title compound was prepare in a manner similar to Example 1(E1) using 4-bromo-N-{5-[cis-3,5-dimethyl-1-piperazinyl]-3-pyridinyl}-3-fluorobenzenesulfonamide (D37) as the starting material. MS (ES$^+$) m/e 445 [M+H]$^+$.

Example 15

N-{5-[cis-3,5-Dimethyl-1-piperazinyl]-2-oxo-1,2-dihydro-3-pyridinyl}-3-fluoro-4-(5-methyl-2-furanyl)benzenesulfonamide

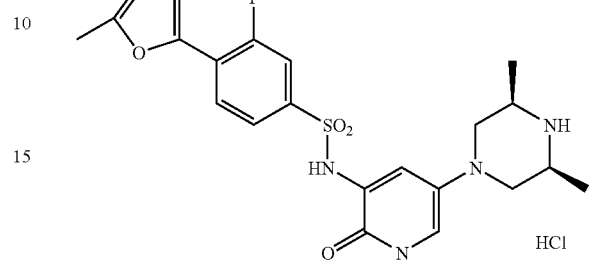

A solution of N-[5-[cis-3,5-dimethyl-4-(phenylmethyl)-1-piperazinyl]-2-(methyloxy)-3-pyridinyl]-3-fluoro-4-(5-methyl-2-furanyl)benzenesulfonamide (D31) 60 mg, 0.1 mmol) in dioxan (2 ml) was treated with 4.0M hydrogen chloride in dioxan (1 ml) and water (0.5 ml). The mixture was heated at 70° C. for 4 hours. The solvent was evaporated and the residue dissolved in ethanol (5 ml) and 2M hydrochloric acid (2 ml). 10% Palladium on carbon (10 mg) was added and the mixture stirred in a hydrogen atmosphere for 4 hours. The mixture was filtered through 'celite' and the solvent was evaporated. Purification by MDAP gave the title compound (E15). MS (ES$^+$) m/e 461 [M+H]$^+$.

Assay Procedures

Cloning of the Ghrelin Receptor GHS-R

Human GHS-R was cloned from human hypothalamus cDNA and TOPO Ta cloned into pCR2.1. The sequence was confirmed and transferred into pCDN for expression analysis. The sequence was confirmed again and the plasmid was electroporated into CHO cells. The clones were screened by FLIPR (Fluorometric Imaging Plate Reader).

Generation of the GHS-R Bacmam Virus and Viral Titre Determination

Virus Generation

The open reading frame of GHS-R was transferred from pCDN into pFastBacmam vector. This vector was used to generate recombinant baculoviruses in which the insect cell-specific polyhedrin promoter has been replaced with a mammalian cell-active promoter, in this case CMV. This was then used with the Bac to Bac expression system (Invitrogen). Briefly the vector was transformed into DH10 bac *E. coli* and the bacmid isolated from the transformed cells. The bacmid was then transfected into Sf9 insect cells grown in ExCell 420 (JRH) medium in 6-well dishes for the production of recombinant baculovirus particles.

The supernatant from these cells was harvested containing the recombinant GHS-R bacmam virus. This P0 viral stock was then used to infect 200 mls of 1×10$^{-6}$ cells/ml Sf9 cells in ExCell 420 medium to further amplify the virus and provide a P1 stock.

This P1 viral stock was then used to amplify a P2 viral stock of 10×1 liter erlemeyer shake flasks again harvesting the supernatant from the cells. This was then used to transduce mammalian cells for assay.

The open reading frame of rat Gαo G-protein was cloned by PCR from rat brain cDNA into pCDNA3 vector. This was then transferred into the pFast Bacmam vector and recombinant baculovirus particles generated as above.

Viral Titre Determination

Viral titres were determined at all stages of the virus scale up with a plaque ELISA method using a gp64 envelope protein monoclonal antibody.

SF9 cells were plated out into a 96 well plate and a dilution range of virus was added to the cells for 1 hour. The virus was removed and a 1% methylcellulose and media mix was added to the cells and incubated for 48 hrs. The cells were then fixed in a formaldehyde and acetone mix for 8 minutes. The cells were then washed with a phosphate buffered saline solution (PBS) and normal goat serum added for 25 mins. This was then removed and a gp64 monoclonal antibody added for 25 mins. The wells were then washed with PBS and a goat anti-mouse/HRP conjugated antibody added for 25 mins. The wells were again washed with PBS and True Blue peroxidase substrate solution (Kirkegaard & Perry Laboratories) added and incubated for 60 mins.

Individual wells were counted for blue foci and taking into account the dilution factor, the plaque forming units/ml of the virus was determined.

1. GHS-R GTPγS Functional Agonist Assay

Generation of Cells Transiently Expressing the Ghrelin Receptor GHS-R

HEK293T cells (HEK293 cells stably expressing the SV40 large T-antigen) were maintained in DMEM containing 10% (v/v) newborn calf serum and 2 mM glutamine. Cells were seeded in 60 mm culture dishes and grown to 60-80% confluency (18-24 hrs) prior to transfection with pCDNA3 containing the relevant DNA species using Lipofectamine reagent. For transfection, 3 µg of DNA was mixed with 10 µl of Lipofectamine in 0.2 mL of Opti-MEM (Life Technologies Inc.) and was incubated at room temperature for 30 min prior to the addition of 1.6 mL of Opti-MEM. For cotransfection experiments, 1.5 µg of each cDNA species was used. Cells were exposed to the Lipofectamine/DNA mixture for 5 hrs and 2 mL of 10% (v/v) newborn calf serum in DMEM was then added. Cells were harvested 48 hrs after transfection.

Generation of Cells Transiently Expressing the Ghrelin Receptor GHS-R and Rat Gαo G-protein.

HEK293F cells maintained in Freestyle media (Invitrogen) were co-transduced with both GHS-R and rat Gαo G-protein by adding 300 mls of GHS-R virus ($1 \times 10^8$ pfu/ml) and 30 mls of Gαo G-protein ($4 \times 10^8$ pfu/ml) to $3 \times 10^8$ HEKF cells in 1 liter of freestyle media. 24 hours post transduction 2 mM sodium butyrate was added to enhance expression. 24 hours post sodium butyrate addition. The cells were harvested by membrane preparation.

Membrane Preparation from Cultured Cells

All steps of the protocol are carried out at 4° C. and with pre-cooled reagents. The cell pellet was resuspended in 10 volumes of buffer A2 containing 50 mM N-2-hydroxyethylpiperazine-N'-2-ethanesulfonic acid (HEPES) (pH 7.40) supplemented with 10e-4M leupeptin (acetyl-leucyl-leucyl-arginal; Sigma L2884), 25 µg/mL bacitracin (Sigma B0125), 1 mM ethylenediamine tetra-acetic acid (EDTA), 1 mM phenylmethylsulfonyl fluoride (PMSF) and 2×10e-6M pepstain A (Sigma). The cells were then homogenised by 2×15 sec bursts in a 1 liter glass Waring blender, followed by centrifugation at 500 g for 20 mins. The supernatant was then spun at 48,000 g for 30 mins. The pellet was resuspended in 4 volumes of buffer A2 by vortexing for 5 secs, followed by homogenisation in a Dounce homogeniser (10-15 strokes). At this point, the preparation was aliquoted into polypropylene tubes and stored at −70° C.

Compounds of the invention were tested for in vitro biological activity in accordance with the following GTPγS assay:

GHS-R GTPγS Functional Agonist Assay Protocol

For each compound being assayed, in an Opti clear bottom 96 well plate, is added:

(a) 5 µl of test compound diluted to required concentration in 100% DMSO and added to 15 µl assay buffer (20 mM N-2-Hydroxyethylpiperazine-N'-2-ethanesulfonic acid (HEPES)+100 mM NaCl+10 mM MgCl$_2$, pH adjusted to 7.4 with NaOH);

(b) 20 µl guanosine 5' [γ35-S] thiotriphosphate, triethylamine salt (Amersham; radioactivity concentration=37 kBq/µl or 1 mCi/ml; Specific Activity 1160 Ci/mmol) diluted to 1.9 nM in assay buffer to give 0.38 nM final.

(c) Membrane (prepared in accordance with the methodology described above) were diluted in assay buffer to give a final concentration which contains 5 µg protein per well in 60 µl. 40 µM final concentration of guanosine 5' diphosphate (GDP) (Sigma; diluted in assay buffer) was added and left to incubate for 10 minutes before addition to the assay The assay is started by the mixing of components from a, b and c and allowed was to incubated at room temperature for 30 mins.

(d) Wheat germ agglutinin-polyvinyltoluene (WGA-PVT) scintillation proximity assay (SPA) beads were diluted in assay buffer to a concentration of 20 mgs/ml.

25 µl of bead was then added to the reaction mix and the assay was incubated for another 30 mins at room temperature with shaking. This was followed by centrifugation for 5 mins at 1500 rpm. The plate was read between 3 and 6 hours after completion of centrifuge run in a Wallac Microbeta counter on a 1 min normalised tritium count protocol. Data was analysed using a 4-parameter logistic equation. Basal activity used as minimum.

The compounds of the Examples had activity of <1 µM in the GHS-R GTPγS functional agonist assays.

2. GHSR Agonist BACMAM FLIPR Assay

Generation of U2OS Cells Transiently Expressing the Ghrelin Receptor GHS-R 24 hours prior to assay U2OS cells at confluence 100% are harvested and spun down. The supernatant is removed and the cells resuspended in media (DMEM+10% FBS+1% L-Glutamine). A cell count is performed using the Cedex instrumentation, and the concentration of cells is adjusted using media to give 20K cells per ml (10K cells/50 ul).

Human GHSR BACMAM virus is added to the cell suspension at an appropriate % volume (calculated for individual batches of BACMAM virus as viral titres vary). The transduced cell suspension is dispensed into FLIPR 384-well clear bottom plates, 50 ul per well. Cell plates are incubated at 37° C. overnight.

Compound Preparation

Master compound plates are prepared in 100% DMSO. 3 mM is the top concentration (giving 10 µM final concentration) and they are serially diluted 1 in 4. 1 ul from the master plate is transferred to a daughter plate, to which is added 50 µl of compound dilution buffer (Tyrodes+1 mg/ml BSA+1.5 mM CaCl$_2$). This plate is used for the assay.

Compounds of the invention were tested for in vitro biological activity in accordance with the following FLIPR assay:

GHSR Agonist BACMAM FLIPR Assay Protocol

Media is aspirated from cell plates using a cell washer (leaving 10 ul of media). Cells are immediately loaded with loading buffer (Tyrodes (Elga water+145 mM NaCl+5 mM KCl+20 mM HEPES+10 mM glucose+1 mM $MgCl_2$)+1.5 mM $CaCl_2$+0.714 mg/ml Probenicid (predissolved in 1M NaOH)+0.5 mM brilliant black+2.5 uM Fluo 4 dye, and incubated at 37.5° C. for 1 hour. 10 µl from compound plates is then added immediately to cell plates using a FLIPR 3 calcium imaging instrument. Fluorescence measurements are taken.

The compounds of the Examples had an $EC_{50}$ value of <1 µM in the GHSR Agonist BACMAM FLIPR Assay.

What is claimed is:

1. The compound N-[6-[cis-3,5-dimethyl-1-piperazinyl]-3-(methyloxy)-2-pyridinyl]-3-fluoro-4-(5-methyl-2-furanyl)benzenesulfonamide.

2. A pharmaceutical composition comprising a compound according to claim 1 and a pharmaceutically acceptable carrier or excipient.

* * * * *